United States Patent

Fujikawa et al.

Patent Number: 4,654,348
Date of Patent: Mar. 31, 1987

[54] PYRAZOLO[4,3-D]PYRIMIDINE DERIVATIVE, PROCESS FOR ITS PRODUCTION, ANTIHYPERLIPIDEMIC AGENT CONTAINING IT, ITS INTERMEDIATE, AND PROCESS FOR THE PRODUCTION OF THE INTERMEDIATE

[75] Inventors: Yoshihiro Fujikawa, Funabashi; Mikio Suzuki, Chiba; Mitsuaki Sakashita, Urawa; Nobutomo Tsuruzoe, Kuki; Tadashi Miyasaka, Yokohama, all of Japan

[73] Assignee: Nissan Chemical Industries Ltd., Tokyo, Japan

[21] Appl. No.: 718,377

[22] Filed: Apr. 1, 1985

[30] Foreign Application Priority Data

Apr. 4, 1984 [JP] Japan ................. 59-67287

[51] Int. Cl.$^4$ .................. A61K 31/415; C07D 487/04
[52] U.S. Cl. ........................ 514/258; 544/262
[58] Field of Search ............. 544/262; 514/258

Primary Examiner—Christine M. Nucker
Assistant Examiner—Robert Benson
Attorney, Agent, or Firm—Oblon, Fisher, Spivak, McClelland & Maier

[57] ABSTRACT

A pyrazolo[4,3-d]pyrimidine derivative having the formula:

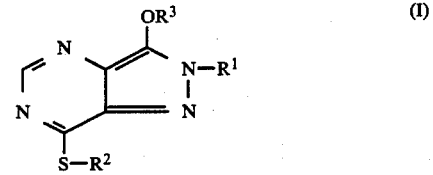

wherein $R^1$ is lower alkyl or phenyl, $R^2$ is —A—$CO_2R^{21}$ (wherein A is alkylene having from 1 to 10 carbon atoms which is unsubstituted or substituted by alkyl having from 1 to 3 carbon atoms; and $R^{21}$ is lower alkyl having from 1 to 4 carbon atoms), —$CH_2CO$-phenyl, a saturated or unsaturated, straight chain or branched aliphatic group having from 3 to 16 carbon atoms, phenyl-lower alkyl, —$CH_2CN$, chloro substituted phenyl-lower alkyl or

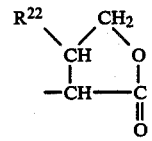

(wherein $R^{22}$ is hydrogen or lower alkyl), and $R^3$ is a saturated or unsaturated, straight chain or branched aliphatic group having from 2 to 22 carbon atoms, phenyl-lower alkyl, benzyloxy substituted phenyl-lower alkyl, lower alkyl substituted or unsubstituted 2-(phenylmethyloxy)ethyl, cyclohexylcyclohexyl, methylcyclohexyl, 3-thia-n-heptyl, 3,6-dioxa-n-decyl, 4-oxo-n-pentyl or 2-hydroxyethyl. Intermediates and processes of making the compounds of formula I are also disclosed. The compounds of formula I are useful as antihyperlipidemic agents.

13 Claims, No Drawings

PYRAZOLO[4,3-D]PYRIMIDINE DERIVATIVE, PROCESS FOR ITS PRODUCTION, ANTIHYPERLIPIDEMIC AGENT CONTAINING IT, ITS INTERMEDIATE, AND PROCESS FOR THE PRODUCTION OF THE INTERMEDIATE

The present invention relates to a novel pyrazolo[4,3-d]pyrimidine derivative, a process for its production, an antihyperlipidemic agent containing it, its intermediate and a process for the production of the intermediate.

Hyperlipidemia (hyperlipemia) is regarded as a major risk factor for the atherosclerosis. Heretofore, a number of antihyperlipidemic agents have been studied. Therapeutic agents in this field are likely to be used for an extended period of time in view of the nature of the diseases, and they are required to be highly safe. However, with respect to nicotinic acid and its derivatives, or clofibrate and its derivatives, which have been widely used as antihyperlipidemic agents, various subsidiary ill effects have been reported, and they can hardly be accepted as satisfactory therapeutic agents. For instance, with respect to nicotinic acid and its derivatives, it has been reported that they will bring about e.g. flashing or gastroenteric troubles. With respect to clofibrate and its derivatives, it is known that they will bring about e.g. myalgia or hepatic insufficiency, and they are likely to lead to gallstone formation. Further, it has been reported that clofibrate brings about hepatic carcinoma on animal experiments. [D. J. Svoboda and D. L. Azarnoff, Cancer Res., 39, 3419 (1979)]

In addition to the question of the safety, there has been a progress in the study of the pharmacological activities. Reflecting the progress in the recent years in the study of the lipid metabolism, particularly in the study of the functional mechanism of serum lipoprotein as a transporter of serum lipid, an attention about the effect of the drug has been drawn not only to the activity of the drug to reduce the lipid concentration in serum but also to the effect to the lipoprotein. Serum cholesterol constitutes the lipoprotein together with triglyceride, phospholipid and apoprotein. This lipoprotein is generally classified into Cyromicron, VLDL (very low density lipoprotein), LDL (low density lipoprotein) and HDL (high density lipoprotein) depending upon the difference in the specific gravity. Among these, Cyromicron, VLDL and LDL are believed to be the lipoproteins which induce atherosclerosis. Whereas, HDL is believed to have functions to transport cholesterol from peripheral blood vessels to a liver, to form a cholesterol ester or to contribute to the catabolism of triglyceride, and thus serves for the prevention and regression of the atherosclerosis. Accordingly, for an antihyperlipidemic agent to be developed, it is desired that such an agent has not only the function to reduce the total value of serum cholesterol, but also the functions to reduce LDL-cholesterol and to increase HDL-cholesterol.

The present inventors have conducted various researches for compounds having antihyperlipidemic effects, and finally found that novel pyrazolo[4,3-d]pyrimidine derivatives of the present invention have excellent antihyperlipidemic effects, and yet they have functions to reduce LDL-cholesterol and increase HDL-cholesterol. Further, they are highly safe without subsidiary ill effects against liver such as hepatomegaly. The present invention has been accomplished on the basis of these discoveries.

The following compounds have been known as the closest to the compounds of the present invention.

Namely, with respect to 3,7-dihydroxy-pyrazolo[4,3-d]pyrimidines with the nitrogen atom at the 2-position substituted by an optionally substituted hydrocarbon group, there have been known only 2-methyl-, phenyl- or substituted phenyl-3,7-dihydroxy-pyrazolo[4,3-d]pyrimidine [H. Ochi and T. Miyasaka, Chem. Pharm. Bull., 31, 1228(1983)] and 2-phenyl-3,5,7-trihydroxy-pyrazolo[4,3-d]pyrimidine [Gerhard Siewert, Arch. Pharm., 278, 327-333(1940)(Chemical Abstract 35, 3232[6])].

3-Ether substituted-pyrazolo[4,3-d]pyrimidine with the nitrogen atom at the 2-position substituted by an optionally substituted hydrocarbon group has not been known.

From the viewpoint of the pharmacological activities, the closest to the compounds of the present invention, with respect to pyrazolo[3,4-d]pyrimidines, is 1H-pyrazolo[3,4-d]pyrimidine-4-amine which is known to have a function to reduce serum lipid [Science, 193,903(1976), J. Lipid Res., 12, 596(1971)]. However, no such an activity has been reported with respect to pyrazolo[4,3-d]pyrimidines.

The present inventors have synthesized novel compounds of the present invention and studied their pharmacological activities, whereupon it has been found that the new compounds have antihyperlipidemic effects. Thus, the present invention has been accomplished.

Namely, the novel pyrazolo[4,3-d]pyrimidines having antihyperlipidemic effects according to the present invention, are represented by the formula:

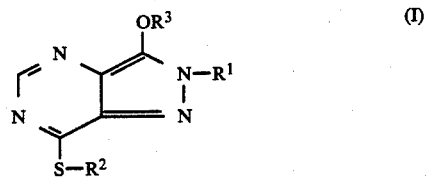

wherein $R^1$ is lower alkyl, phenyl or substituted phenyl, $R^2$ is -A-$CO_2R^{21}$ (wherein A is alkylene having from 1 to 10 carbon atoms which is unsubstituted or substituted by alkyl having 1 to 3 carbon atoms, and $R^{21}$ is lower alkyl having from 1 to 4 carbon atoms), —$CH_2$CO-phenyl, a saturated or unsaturated, straight chain or branched aliphatic group having from 3 to 16 carbon atoms, phenyl-lower alkyl, —$CH_2$CN, substituted phenyl-lower alkyl, or

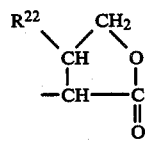

(wherein $R^{22}$ is hydrogen or lower alkyl), and $R^3$ is a saturated or unsaturated, straight chain or branched aliphatic group having from 2 to 22 carbon atoms, phenyl-lower alkyl, benzyloxy substituted phenyl-lower alkyl, lower alkyl substituted or unsubstituted phenylmethyloxyethyl cyclohexycyclohexyl, methylcyclohexyl, 3-thia-n-heptyl, 3, 6-dioxa-n-decyl, 4-oxo-n-pentyl or 2-hydroxyethyl.

The present invention also provides an antihyperlipidemic agent which comprises an effective amount of the pyrimidine derivative of the formula I as defined above and a pharmaceutically acceptable carrier.

The pyrimidine derivative of the formula I of the present invention is produced by a process which comprises reacting a pyrazolo[4,3-d]pyrimidine derivative having the formula:

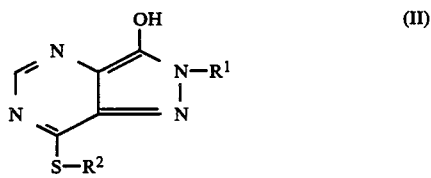

wherein $R^1$ and $R^2$ are as defined above, with $R^3X$ wherein $R^3$ is as defined above and X is halogen, alkylsulfonyloxy or unsubstituted or substituted phenylsulfonyloxy, in the presence of an acid binding agent.

Further, the intermediate of the formula II is also a novel compound according to the present invention, and is prepared by a process which comprises reacting a pyrazolo[4,3-d]pyrimidine derivative having the formula:

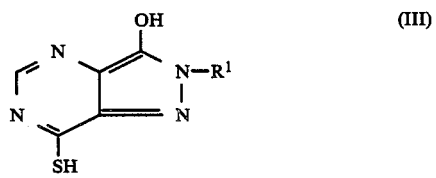

wherein $R^1$ is as defined above, with $R^2X$ wherein $R^2$ is as defined above and X is halogen, alkylsulfonyloxy or unsubstituted or substituted phenylsulfonyloxy, in the presence of an acid binding agent.

Now, the present invention will be described in detail with reference to the preferred embodiments.

The overall process for the production of pyrazolo[4,3-d]pyrimidines of the formula I according to the present invention is represented by the following process steps.

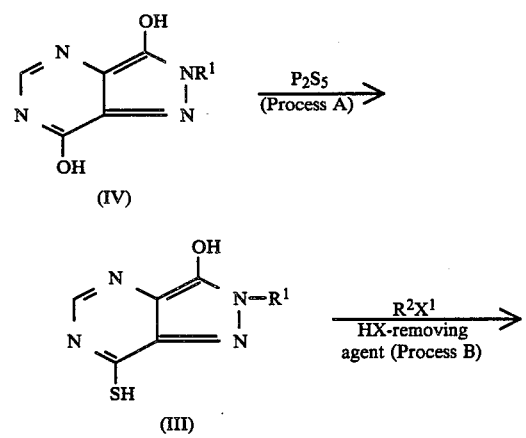

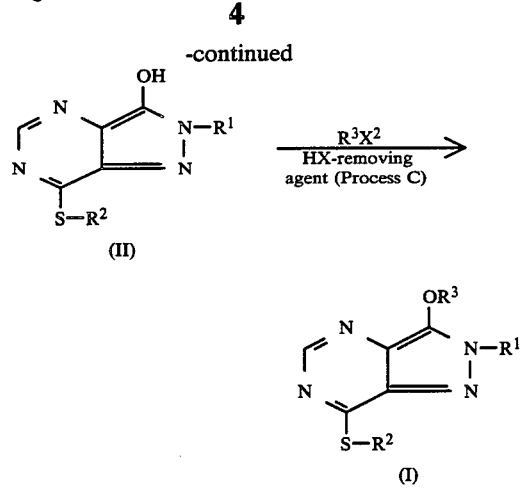

In the above reaction formulas, each of $X^1$ and $X^2$ is halogen, alkylsulfonyloxy or phenylsulfonyloxy which may optionally be substituted by lower alkyl such as methyl or halogen such as chlorine, and $R^1$, $R^2$ and $R^3$ are as defined above with respect to the formula I.

Process A is a process step to convert the hydroxy group at the 7-position of 3,7-dihydroxy pyrazolo[4,3-d]pyrimidine to a mercapto group. This reaction is conducted in an organic solvent such as pyridine by reacting phosphorus pentasulfide under heating.

Process B is a step of preparing a thioether compound by the reaction of the mercapto group at the 7-position with a halide, an optionally substituted phenylsulfonyloxy compound or an alkylsulfonyloxy compound. This reaction is conducted in water or an alcoholic organic solvent such as methanol or ethanol, or in a mixture of such solvents, at room temperature or under heating, in the presence of an acid binding agent such as sodium carbonate or potassium carbonate. Alternatively, the reaction may be conducted in aqueous ammonia at room temperature.

Process C is a step of forming an ether bond by the reaction of the hydroxy group at the 3-position with a halide, an optionally substituted phenylsulfonyloxy compound or an alkylsulfonyloxy compound. This reaction is conducted in an organic solvent such as benzene, toluene, xylene, dimethylformamide, dimethylacetamide, dimethylsulfoxide, dioxane, tetrahydrofuran, methanol or ethanol, at room tempeature or under heating in the presence of an acid binding agent such as potassium carbonate, sodium carbonate, a tertiary amine or pyridine. Alternatively, the reaction may be conducted in a solvent mixture comprising water and an organic solvent hardly soluble in water such as chloroform, methylene chloride, benzene or toluene or a mixture of such organic solvents, in the presence of an acid binding agent such as potassium carbonate, sodium carbonate, sodium hydroxide or potassium hydroxide and, if necessary, a phase transfer catalyst such as 18-crown-6.

The compound of the formula II obtained by Process B is novel. This compound is industrially useful, since it is an intermediate material, from which the compound of the formula I having antihyperlipidemic effects can directly be obtained as shown by Process C.

The compounds of the formula I of the present invention have remarkable antihyperlipidemic effects, and may be formulated into various suitable formulations depending upon the manner of the administration.

The pharmaceutical composition of the present invention comprises an effective amount of the compound of the formula I and a pharmaceutically acceptable carrier. The effective amount is usually at least 5% by weight, based on the total composition. As the pharmaceutically acceptable carrier, there may be mentioned a pharmaceutically acceptable binder such as a syrup, gum arabic, gelatin, sorbitol, tragacanth gum or polyvinylpyrrolidone (molecular weight of e.g. about 25,000); an excipient such as lactose, sugar, corn starch, calcium phosphate, sorbitol or glycine; a lubricant such as magnesium stearate, talc, polyethylene glycol or silica; or a disintegrator such as potato starch. By properly selecting the carrier, the pharmaceutical composition of the present invention may be formulated into powders, granules, tablets or capsules. It is preferably administered orally. However, the manner of administration is not restricted to oral administration, and non-oral administration such as percutaneous administration, injection (through an intravenous, subcutaneous or intramuscular route) or rectal administration may be employed. For instance, it may be administered as a suppository as combined with oily base material such as cacao butter, polyethylene glycol, lanolin or fatty acid triglyceride.

The daily dose of the compound of the formula I is from 0.01 to 2.0 g, preferably from 0.1 to 1.5 g, for an adult. It is administered from once to three times per day. The dose may of course be varied depending upon the age, the weight or the condition of illness of the patient.

Now, the present invention will be described in further detail with reference to test examples for the antihyperlipidemic effects of the compounds of the formula I, working examples for the synthesis of the intermediates of the formula II, working examples for the synthesis of the compounds of the formula I and formulation examples for the antihyperlipidemic agent.

In the following description, Me means methyl; Et means ethyl; Pr means propyl; Bu means butyl; and Ph means phenyl.

Test 1

The antihyperlipidemic activity in emulsion-induced hyperlipidemic rats:

Male S.D. rats weighing 80-90 g (4 weeks old) were used. They were divided into groups of 5 to 6 rats each. The test compounds suspended in 0.5% CMC-Na(carboxymethyl cellulose sodium salt) were given to the rats in a daily dose of 4 ml/kg (i.e. 300 mg/kg of the test compounds) via stomach tube every 10:00 a.m. After 30 min., lipids emulsion having the following composition was orally given to the rats in an amount of 2.5 ml per rat.

| Composition of emulsion: | |
| --- | --- |
| Cholesterol | 22.5 g |
| Cholic acid sodium salt | 10.0 g |
| Sucrose | 90.0 g |
| Olive oil | 150.0 g |
| Water | x ml |
| Final volume | 300.0 ml |

During the experimental period of 3 days, the rats were fed on a standard commercial diet and water ad libitum. At the end of the period, the rats were fasted for 16 hours and then blood samples were obtained from inferior vena cava. The total cholesterol and HDL cholesterol were measured.

The weight of the liver was measured. To the control group, only the aqueous CMC-Na solution and the lipids emulsion were given.

The fractionation of lipoproteins was conducted by a dextran sulfate-$MgCl_2$ precipitation method.

Cholesterol in serum was measured by means of a cholesterol measuring kit (Cholesterol C-Test Wako, manufactured by Wako Junyaku Co., Ltd.), and cholesterol in HDL was measured by means of NC Hi-Set, manufactured by Nippon Chemiphar Co., Ltd.

In the following description, cholesterol is referred to as "Chol".

Further, the reduction rate of Chol was calculated by the following equation.

$$\text{Reduction rate (\%)} = \frac{A - B}{A} \times 100$$

where A is the amount of serum Chol (mg/dl) of the control group, and B is the amount of serum Chol (mg/dl) of the group to which the therapeutic agent was administered.

Likewise, the increase rate of HDL-Chol was calculated by the following equation.

$$\text{Increase rate (\%)} = \frac{D - C}{C} \times 100$$

where C is the amount of serum HDL-Chol (mg/dl) of the control group, and D is the amount of serum HDL-Chol (mg/dl) of the group to which the therapeutic agent was administered.

The degree of hepatomegaly (i.e. the change rate of the liver weight) was calculated by the following equation.

$$\text{Degree of hepatomegaly (\%)} = \frac{F - E}{E} \times 100$$

where E is the liver weight (g) per 100 g of the body weight of the control group, and F is the liver weight (g) per 100 g of the body weight of the group to which the therapeutic agent was administered.

The test results are shown in Tables 1 and 2.

TABLE 1

The effects of the compounds of the formula I for the reduction of serum Chol

| Example No. | $R^1$ | $R^2$ | $R^3$ | Reduction rate of serum Chol. (%) |
| --- | --- | --- | --- | --- |
| 1 | —Me | —$CH_2CO_2Et$ | —$C_{16}H_{33}$—n | 58 |
| 2 | " | " | —$C_{12}H_{25}$—n | 36 |
| 3 | " | " | —$C_{14}H_{29}$—n | 41 |
| 4 | " | " | —$C_{15}H_{31}$—n | 48 |

TABLE 1-continued

The effects of the compounds of the formula I for the reduction of serum Chol

| Example No. | $R^1$ | $R^2$ | $R^3$ | Reduction rate of serum Chol. (%) |
|---|---|---|---|---|
| 5 | " | " | $-C_{17}H_{35}-n$ | 21 |
| 6 | " | " | $-C_{18}H_{37}-n$ | 31 |
| 8 | " | " | $-C_{20}H_{41}-n$ | 37 |
| 9 | " | " | $-C_{18}H_{35}$ (oleyl) | 66 |
| 10 | " | " | $-C_{18}H_{33}$ (linoleyl) | 76 |
| 11 | " | " | $-C_{18}H_{31}$ (linoleyl) | 83 |
| 15 | " | $-CH_2CO_2Me$ | $-C_{16}H_{33}-n$ | 53 |
| 16 | " | $-CH_2CO_2Pr-i$ | " | 26 |
| 17 | " | $-(CH_2)_3CO_2Et$ | " | 49 |
| 18 | " | $-CH_2COPh$ | " | 35 |
| 19 | " | $-CH_2Ph$ | " | 42 |
| 20 | " | 3,4-di-chloro-phenylmethyl- | " | 19 |
| 21 | " | $-CH_2CH_2Ph$ | " | 10 |
| 22 | " | $-CH_2CH=CH_2$ | " | 11 |
| 23 | " | $-C_6H_{13}-n$ | " | 39 |
| 24 | " | $-C_{16}H_{33}-n$ | " | 41 |
| 25 | " | 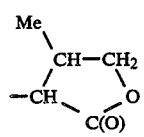 | " | 11 |
| 26 | " | $-C(CH_3)_2CO_2Et$ | " | 16 |
| 27 | " | " | $-C_8H_{17}-n$ | 16 |
| 28 | " | " | $-C_{12}H_{25}-n$ | 36 |
| 29 | " | " | $-C_{20}H_{41}-n$ | 16 |
| 30 | " | " | $-CH_2CH_2OH$ | 28 |
| 31 | $-Ph$ | $-CH_2CO_2Et$ | $-C_7H_{15}-n$ | 51 |
| 32 | " | $-C(CH_3)_2CO_2Et$ | $-C_{12}H_{25}-n$ | 50 |
| 33 | $-Me$ | $-CH_2CO_2Bu-n$ | $-C_{16}H_{33}-n$ | 39 |
| 34 | " | $-CH_2CO_2Et$ | 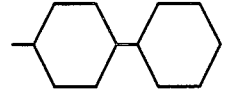 | 12 |
| 35 | " | " | 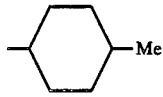 | 13 |
| 36 | " | " | $-CH_2CH_2OCH_2Ph$ | 44 |
| 37 | " | " | 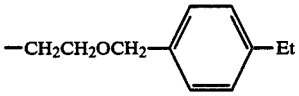 $-CH_2CH_2OCH_2\text{-C}_6H_4\text{-}Et$ | 37 |
| 38 | " | " | 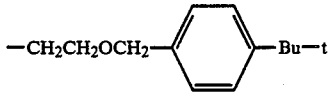 $-CH_2CH_2OCH_2\text{-C}_6H_4\text{-}Bu\text{-}t$ | 15 |
| 39 | " | " | $-(CH_2CH_2O)_2(CH_2)_3CH_3$ | 11 |
| 40 | " | " | $-(CH_2CH_2CH(CH_3)-CH_2)_4-H$ | 50 |
| 41 | " | " | $-(CH_2CH_2CH(CH_3)-CH_2)_3-H$ | 48 |
| 42 | " | " | $-C_8H_{17}-n$ | 32 |
| 43 | " | " | $-CH(CH_3)(CH_2)_{13}CH_3$ | 28 |
| 44 | " | " | $-(CH_2)_8C\equiv C(CH_2)_7CH_3$ | 39 |

TABLE 1-continued

The effects of the compounds of the formula I for the reduction of serum Chol

| Example No. | $R^1$ | $R^2$ | $R^3$ | Reduction rate of serum Chol. (%) |
|---|---|---|---|---|
| 45 | " | " | $-(CH_2)_8CH=CH_2$ | 22 |
| 46 | " | " | $-(CH_2)_3\overset{O}{\overset{\|}{C}}CH_3$ | 11 |
| 47 | —Ph | " | $-(CH_2)_2CH=CHCH_2CH_3$ | 10 |
| 48 | " | " | $-(CH_2)_2OCH_2-\phantom{x}\text{C}_6H_4\text{-Bu-t}$ | 34 |
| 49 | " | " | $-(CH_2)_2S(CH_2)_3CH_3$ | 14 |
| 50 | " | " | $-C_{18}H_{35}$ (oleyl) | 35 |
| 51 | " | " | $-(CH_2)_8CH=CH_2$ | 58 |
| 52 | " | " | $-C_{16}H_{33}-n$ | 30 |
| 53 | " | " | $-(CH_2)_2CH=CH(CH_2)_2CH_3$ | 11 |
| 54 | —Me | $-CH_2CO_2Me$ | $-C_{18}H_{33}$ (linoleyl) | 79 |
| 55 | " | $-C_6H_{13}-n$ | " | 58 |
| 56 | " | $-CH_2CO_2Bu-n$ | " | 60 |
| 57 | " | $-CH_2CN$ | " | 61 |
| 58 | " | $-\underset{CH_3}{\overset{}{C}}HCO_2Et$ | " | 32 |
| 59 | " | $-(CH_2)_3CO_2Et$ | " | 68 |
| 60 | " | $-(CH_2)_4CO_2Et$ | " | 22 |
| 61 | " | $-(CH_2)_{10}CO_2Et$ | " | 35 |
| 62 | " | $-CH_2Ph$ | " | 17 |
| 63 | " | $-\underset{Pr-i}{\overset{}{C}}HCO_2Et$ | " | 39 |
| 64 | " | $-CH_2CH=CH_2$ | " | 12 |
| 69 | " | $-CH_2CO_2Et$ | $-C_{22}H_{43}$ (erucyl) | 59 |
| 70 | " | " | $-C_{18}H_{35}$ (elaidyl) | 63 |
| 71 | " | " | $-C_{18}H_{35}$ (petroselinyl) | 64 |
| 72 | " | " | $-C_{18}H_{35}$ (vaccenyl) | 58 |
| 73 | " | " | $-(CH_2)_9CH=CH_2$ | 27 |
| 74 | " | " | $-(CH_2)_2C≡C(CH_2)_5CH_3$ | 16 |
| Clofibrate* (Reference compound) | | | | 44 |

*Clofibrate

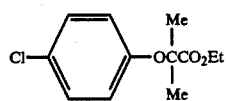

TABLE 2

The effects of the compounds of the formula I over the serum HDL-Chol and the liver weight

| Example No. | $R^1$ | $R^2$ | $R^3$ | Increase rate of serum HDL-Chol (%) | Degree of hepato-megaly (%) |
|---|---|---|---|---|---|
| 1 | —Me | $-CH_2CO_2Et$ | $-C_{16}H_{33}-n$ | 42 | +8 |
| 4 | " | " | $-C_{15}H_{31}-n$ | 20 | +2 |
| 5 | " | " | $-C_{17}H_{35}-n$ | 38 | +3 |
| 6 | " | " | $-C_{18}H_{37}-n$ | 9 | −1 |
| 9 | " | $-CH_2CO_2Et$ | $-C_{18}H_{35}$ (oleyl) | 55 | +5 |
| 10 | " | " | $-C_{18}H_{33}$ (linolenyl) | 13 | +12 |
| 11 | " | " | $-C_{18}H_{31}$ (linolenyl) | 26 | +20 |
| 17 | " | $-(CH_2)_3CO_2Et$ | $-C_{16}H_{33}-n$ | | +5 |
| 18 | " | $-CH_2COPh$ | " | 42 | +4 |
| 19 | " | $-CH_2Ph$ | " | 31 | +8 |
| 23 | " | $-C_6H_{13}-n$ | " | 30 | 0 |
| Clofibrate* | | | | 12 | +22 |

*see the footnote of Table 1

Test 2: Acute toxicity

The test compounds suspended in 0.5% CMC-Na were administered p.o. to male ddY mice. The acute toxicity was determined based on the mortality after seven days. In respect of the compounds of Examples 1, 9, 10 and 11 of the present invention, the mortality was 0% even at a dose of as high as 8000 mg/kg by oral administration.

EXAMPLE A-1

2-Methyl-3-hydroxy-7-ethoxycarbonylmethylthio-pyrazolo[4,3-d]pyrimidine

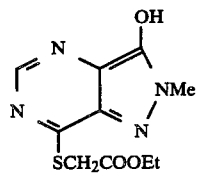

10 g of 2-methyl-3-hydroxy-7-mercapto-pyrazolo[4,3-d]pyrimidine and 8.36 g of anhydrous potassium carbonate were dissolved in 100 ml of water, and after an addition of 8.08 g of ethyl bromoacetate, the mixture was stirred at room temperature for 4 hours. After confirming the completion of the reaction by means of thin layer chromatography, the reaction mixture was shaken with chloroform, whereby by-products were extracted to the chloroform layer and thus removed. The aqueous layer was neutralized with 1:1 hydrochloric acid to bring the pH to a level of from 3 to 4. The precipitated crystals were collected by filtration and then washed with water. Then, the crystals were recrystallized from acetone.

Yield: 9.24 g (62.7%), yellow crystals.
Melting point: 178°–182° C.
pmr (CDCl$_3$) δppm: 1.25 (t, 3H, J=8 Hz), 4.0 (s, 3H), 4.13 (s, 2H), 4.20 (q, 2H, J=8 Hz) 8.43 (s, 1H), 10.3 (s, 1H).

EXAMPLE A-2

2-Methyl-3-hydroxy-7-isopropoxycarbonylmethylthio-pyrazolo[4,3-d]pyrimidine

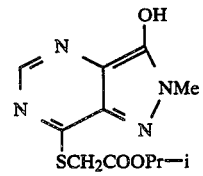

The reaction and treatment were conducted in the same manner as in Example A-1 except that isopropyl bromoacetate was used instead of ethyl bromoacetate used in Example A-1, whereby the desired compound was obtained.

Yield: 61.6%.
Melting point: 192.5°–194.0° C. (as recrystallized from acetone), orange powder.
pmr (CDCl$_3$) δppm: 1.25 (d, 6H, J=6.2 Hz), 4.03 (s, 3H) 4.12 (s, 2H), 5.08 (hept, 1H, J=6.2 Hz), 8.44 (s, 1H).

EXAMPLE A-3

2-Methyl-3-hydroxy-7-methoxycarbonylmethylthio-pyrazolo[4,3-d]pyrimidine

1.5 g of 2-methyl-3-hydroxy-7-mercapto-pyrazolo[4,3-d]pyrimidine was suspended in 35 ml of methanol, and 1.25 g of anhydrous potassium carbonate and 1.07 g of methyl chloroacetate were sequentially added. The mixture was heated at 60° C. for 18 hours. Then, the solvent was distilled off. Water was added to the residue, and the residue was dissolved. Chloroform-soluble substances were extracted with chloroform and removed. Then, the aqueous layer was acidified with 1:1 hydrochloric acid, and the precipitated solid was extracted with chloroform. This chloroform layer was washed with water, and dried over anhydrous magnesium sulfate. Then, the solvent was distilled off. The remaining solid was recrystallized from acetone-chloroform.

Yield: 0.93 g (44.4%), orange powder.
Melting point: 195°–196° C.
pmr (CDCl$_3$) δppm: 3.78 (s, 3H), 4.04 (s, 3H), 4.24 (s, 2H), 8.58 (s, 1H).

EXAMPLE A-4

2-Phenyl-3-hydroxy-7-(1-ethoxycarbonyl-1-methylethylthio)-pyrazolo[4,3-d]pyrimidine

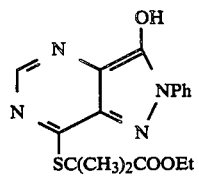

3.66 g of 2-phenyl-3-hydroxy-7-mercapto-pyrazolo[4,3-d]pyrimidine was suspended in a solvent mixture comprising 150 ml of ethanol and 30 ml of water, and 2.5 g of anhydrous potassium carbonate was added thereto. While heating the mixture to 80° C., 3.5 g of ethyl α-bromoisobutyrate was dropwise added thereto, and the heating was continued for further 6 hours. Then, the solvent was distilled off. Water was added to the residue and the residue was dissolved. The solution was acidified with hydrochloric acid, and then extracted with chloroform. The starting material insoluble in both the aqueous layer and the chloroform layer was collected by filtration and recovered (recovered amount: 1.5 g). The chloroform layer was dried over anhydrous magnesium sulfate, and then the solvent was distilled off. The remaining solid was recrystallized from acetone.

Yield: 1.43 g (45%).
Melting point: 185°–186° C.
pmr (CDCl$_3$) δppm: 1.18 (t, 3H, J=6.8 Hz), 1.81 (s, 2H), 4.18 (q, 2H, J=6.8 Hz), 7.37–8.17 (m, 5H), 8.40 (s, 1H), 8.87 (br. s, 1H).

EXAMPLE A-5

2-Methyl-3-hydroxy-7-(1-ethoxycarbonyl-1-methylethylthio)-pyrazolo[4,3-d]pyrimidine

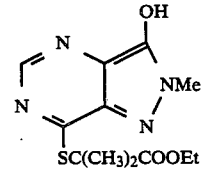

The reaction and treatment were conducted in the same manner as in Example A-4 except that 2-methyl-3-hydroxy-7-mercapto-pyrazolo[4,3-d]pyrimidine was used instead of 2-phenyl-3-hydroxy-7-mercapto-pyrazolo[4,3-d]pyrimidine used in Example A-4, whereby the desired product was obtained.

Yield: 38.3%.

Melting point: 155°–156° C. (as recrystallized from acetone).

pmr (CDCl$_3$) δppm: 1.20 (t, 3H), 1.85 (s, 6H), 4.05 (s, 3H), 4.20 (q, 2H, J=6 Hz), 8.65 (s, 1H), 11.0 (br. s, 1H).

Mass (m/e): 295 (M$^+$−1) 250 (M$^+$−OEt), 182 [M$^+$−CH$_2$=C(CH$_3$)COOEt].

EXAMPLE A-6

2-Phenyl-3-hydroxy-7-ethoxycarbonylmethylthio-pyrazolo[4,3-d]pyrimidine

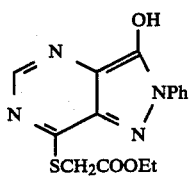

1.22 g of 2-phenyl-3-hydroxy-7-mercapto-pyrazolo[4,3-d]pyrimidine was suspended in 100 ml of ethanol, and 0.5 g of potassium hydrogen carbonate was added. While heating the mixture at 80° C., 1 g of ethyl bromoacetate was dropwise added, and the heating and reaction were continued for further 2 hours. Then, the solvent was distilled off. Water was added to the residue, and the residue was dissolved. The solution was acidified with hydrochloric acid, and the precipitated crystals were extracted with chloroform. The chloroform layer was dried over anhydrous magnesium sulfate, and the solvent was distilled off. The remaining solid was recrystallized from acetone-chloroform.

Yield: 0.71 g (43%).

Melting point: 181°–183° C.

pmr (CDCl$_3$) δppm: 1.29 (t, 3H), 4.20 (s, 2H), 4.24 (q, 2H, J=7 Hz), 7.17 (br. s, 1H), 7.28–8.11 (m, 5H), 8.50 (s, 1H).

EXAMPLE A-7

2-Methyl-3-hydroxy-7-n-hexadecylthio-pyrazolo[4,3-d]pyrimidine

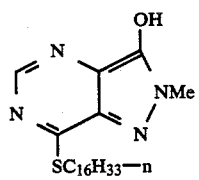

3.64 g of 2-methyl-3-hydroxy-7-mercapto-pyrazolo 4,3-d]pyrimidine was suspended in 200 ml of ethanol, and 3.04 g of anhydrous potassium carbonate was added. Further, 7.33 g of cetyl bromide was added, and the mixture was refluxed at 90° C. for 7.5 hours. Ethanol was distilled off, and water was added to the residue. The solution thereby obtained was acidified with hydrochloric acid, and then extracted with chloroform. The chloroform layer was separated, washed with water, and dried over anhydrous magnesium sulfate, and then chloroform was distilled off. The remaining solid was recrystallized from chloroform.

Yield: 45%, yellow crystals.

Melting point: 132.5°–133° C.

Mass (m/e): 406 (M$^+$), 182 (M$^+$−C$_{16}$H$_{32}$).

EXAMPLE A-8

2-Methyl-3-hydroxy-7-[3-(ethoxycarbonyl)propylthio]-pyrazolo[4,3-d]pyrimidine

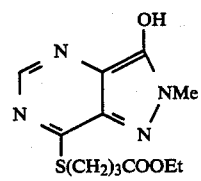

The reaction and treatment were conducted in the same manner as in Example A-7 except that ethoxycarbonylpropyl bromide was used instead of cetyl bromide used in Example A-7, whereby the desired product was obtained.

Yield: 55%.

Melting point: 160°–161° C. (as recrystallized from ethyl acetate), orange fluffy crystals.

pmr (CDCl$_3$) δppm: 1.26 (t, 3H), 2.14 (m, 2H), 2.50 (t, 2H, J=8 Hz), 3.47 (t, 2H, J=8 Hz), 4.03 (s, 3H), 4.15 (q, 2H, J=7 Hz), 8.46 (s, 1H), 9.10 (br. s, 1H).

Mass (m/e): 295 (M$^+$−1) 223 (M$^+$−COOEt), 182 (M$^+$−CH$_2$=CHCH$_2$COOEt).

EXAMPLE A-9

2-Methyl-3-hydroxy-7-[4-(3-methyl-5-oxo-tetrahydrofuranyl)thio-pyrazolo[4,3-d]pyrimidine

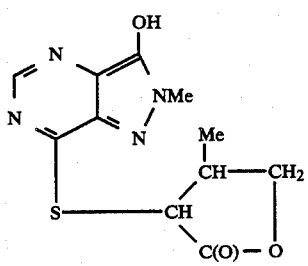

The reaction and treatment were conducted in the same manner as in Example A-7 except that α-bromo-γ-valerolactone instead of cetyl bromide used in Example A-7, whereby the desired product was obtained.

Yield: 28%.

Melting point: 168°–170° C. (as recrystallized from acetone), orange crystals.

pmr (CDCl$_3$-d$_6$-DMSO) δppm: 1.50, 1.54 (d, 3H, J=7 Hz), 2.15–2.98 (m, 2H), 3.89 (s, 3H), 4.56–5.13 (m, 1H), 8.61 (s, 1H) (a mixture of lactone-ring methyl stereoisomers).

EXAMPLE A-10

2-Methyl-3-hydroxy-7-n-butylthio-pyrazolo[4,3-d]pyrimidine

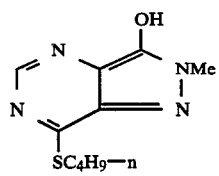

1.2 g of 2-methyl-3-hydroxy-7-mercapto-pyrazolo[4,3-d]pyrimidine was dissolved in 50 ml of aqueous ammonia, and after an addition of 1.08 g of n-butyl bromide, the mixture was stirred at room temperature for 5 hours. By means of a rotary evaporator, ammonia gas was distilled off at room temperature. Then, the aqueous solution was acidified with hydrochloric acid and extracted with chloroform. The chloroform layer was dried over anhydrous magnesium sulfate, and then evaporated to dryness. The remaining solid was recrystallized from acetone.

Yield: 38%, orange solid.
Melting point: 184.0°–184.5° C.

EXAMPLES A-11 to A-16

The following compounds of Examples A-11 to A-16 were prepared by the same reaction and treatment as in Example A-10 except that instead of n-butyl bromide used in Example A-10, other halogen compounds as specified below were used as the respective starting materials.

EXAMPLE A-11

2-Methyl-3-hydroxy-7-benzylthio-pyrazolo[4,3-d]pyrimidine

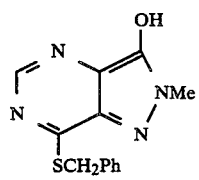

Starting compound: Benzyl bromide.
Yield: 25%.
Melting point: 197°–199°C. (as recrystallized from ethanol), orange crystals.
pmr (d$_6$-DMSO) δppm: 3.80 (s, 3H), 4.65 (s, 2H), 7.2–7.7 (m, 5H), 8.7 (s, 1H).

EXAMPLE A-12

2-Methyl-3-hydroxy-7-(3,4-dichlorophenylmethylthio)-pyrazolo[4,3-d]pyrimidine

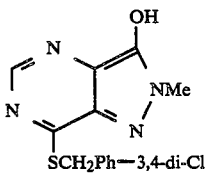

Starting compound: 3,4-Dichlorophenylmethyl chloride.

Yield: 81%.
Melting point: 252°–254.5° C. (as recrystallized from chloroform-ethanol), reddish orange powder.
pmr (d$_6$-DMSO) δppm: 3.74 (s, 3H), 4.63 (s, 2H), 7.4–7.7 (m, 3H), 8.57 (s, 1H).

EXAMPLE A-13

2-Methyl-3-hydroxy-7-phenethylthio-pyrazolo[4,3-d]pyrimidine

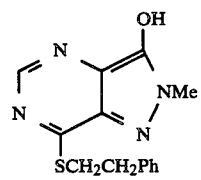

Starting compound: Phenethyl bromide.
Yield: 76%.
Melting point: 225°–227° C. (as recrystallized from chloroform), reddish orange powder.
pmr (d$_6$-DMSO) δppm: 2.8–3.2, 3.4–3.7 (m, 2H×2), 3.72 (s, 3H), 7.25 (m, 5H), 8.62 (s, 1H).

EXAMPLE A-14

2-Methyl-3-hydroxy-7-benzoylmethylthio-pyrazolo[4,3-d)pyrimidine

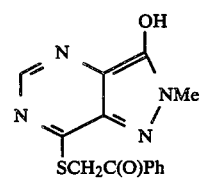

Starting compound: Phenacyl bromide.
Yield: 39%.
Melting point: 179° C. (as recrystallized from methanol), reddish orange powder.
pmr (d$_6$-DMSO) δppm: 3.78 (s, 3H), 5.02 (s, 2H), 7.4–7.8, 8.0–8.2 (m, 3H+2H), 8.42 (s, 1H).
Mass (m/e): 300 (M+), 268 (M+—S), 195 (M+—COPh).

EXAMPLE A-15

2-Methyl-3-hydroxy-7-allylthio-pyrazolo[4,3-d]pyrimidine

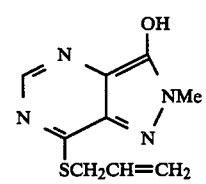

Starting compound: Allyl bromide.
Yield: 54%.
Melting point: 213°–214° C. (as recrystallized from acetone), reddish orange powder.
pmr (d$_6$-DMSO) δppm: 3.80 (s, 3H), 4.05 (d, 2H, J=6 Hz), 5.0–5.6 (m, 2H), 5.7–6.4 (m, 1H), 8.65 (s, 1H).

EXAMPLE A-16

2-Methyl-3-hydroxy-7-n-hexylthio-pyrazolo[4,3-d]pyrimidine

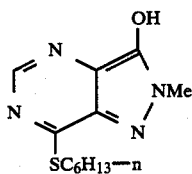

Starting compound: n-Hexyl bromide.
Yield: 47%.
Melting point: 163°–164° C. (as recrystallized from acetone), orange needle-like crystals.
pmr (CDCl$_3$) δppm: 0.90 (t, 3H), 1.0–2.0 (m, 8H), 3.40 (t, 2H, J=b 7 Hz), 4.02 (s, 3H), 8.46 (s, 1H).
Mass (m/e): 266 (M+), 182 (M+—C$_6$H$_{12}$).

EXAMPLE A-17

2-Methyl-3-hydroxy-7-n-butoxycarbonylmethylthio-pyrazolo[4,3-d]pyrimidine

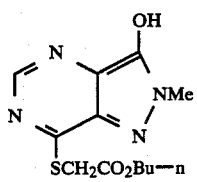

The reaction and treatment were conducted in the same manner as in Example A-1 except that n-butyl bromoacetate was used instead of ethyl bromoacetate used in Example A-1, whereby the desired product was obtained.
Yield: 45.3%.
Melting point: 171.5°–172° C. (as recrystallized from chloroform-acetone), reddish orange needle-like crystals.
pmr (CDCl$_3$) δppm: 0.9 (t, 3H), 1.2–1.9 (m, 4H), 4.0 (s, 3H), 4.15 (s, 2H), 4.0–4.4 (m, 2H), 8.4 (s, 1H), 10.8 (s, 1H).

EXAMPLE A-18

2-Methyl-3-hydroxy-7-cyanomethylthio-pyrazolo[4,3-d]pyrimidine

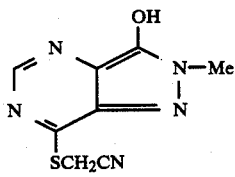

The reaction and treatment were conducted in the same manner as in Example A-10 except that chloroacetonitrile was used instead of n-butyl bromide used in Example A-10, whereby the desired product was obtained.
Yield: 23%.
Melting point: 205° C. (decomposed)(as recrystallized from ethanol-acetone), orange powder.
pmr (d$_6$-DMSO) δppm: 3.84 (s, 3H), 4.42 (s, 2H), 8.60 (s, 1H), 0.70 (br. s, 1H).

EXAMPLE A-19

2-Methyl-3-hydroxy-7-(1-ethoxycarbonylethylthio)-pyrazolo[4,3-d]pyrimidine

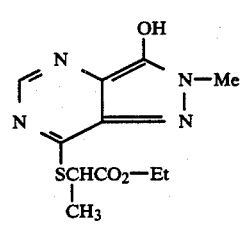

The reaction and treatment were conducted in the same manner as in Example A-7 except that ethyl α-bromopropionate was used instead of cetyl bromide used in Example A-7, whereby the desired product was obtained.
Yield: 47%.
Melting point: 127°–131° C. (as recrystallized from aceton), orange powder.
pmr (CDCl$_3$) δppm: 1.29 (t, 3H, J=8 Hz), 1.73 (d, 3H, J=7 Hz), 4.03 (s, 3H), 4.25 (q, 2H, J=7 Hz), 4.92 (q, 1H, J=7 Hz), 8.49 (s, 1H), 10.9 (br. s, 1H).

EXAMPLE A-20

2-Methyl-3-hydroxy-7-mercapto-pyrazolo[4,3-d]pyrimidine

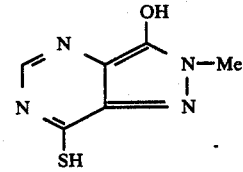

50 g of 2-methyl-3,7-dihydroxy-pyrazolo[4,3-d]pyrimidine was suspended in 500 ml of dried pyridine. Then, 140 g of phosphorus pentasulfide was gradually added while thoroughly stirring the suspension. After the termination of the heat generation, stirring was continued until the solution temperature became close to room temperature. Then, the mixture was heated and stirred at a temperature of from 80° to 100° C. for about 1.5 hours, whereby a uniform brown solution was obtained. Pyridine was distilled off under reduced pressure. Then, 500 ml of water was added to the remaining viscous oily substance, and the mixture was shaked to obtain a uniform solution. The solution was then heated for 1.5 hours on a hot bath. The mixture was cooled and acidified with hydrochloric acid. The precipitates were collected by filtration, and washed with water to obtain yellowish brown powder. This powder was dissolved in a saturated sodium bicarbonate aqueous solution, and the insoluble substance was removed by filtration. The filtrate was acidified with hydrochloric acid, and the precipitated yellowish brown powder was collected by filtration, washed with water and then dried.
Yield: 36 g (60%).
Melting point: >320° C.
pmr (d$_6$-DMSO) δppm: 3.70 (s, 3H), 7.80 (s, 1H).

EXAMPLE A-21

2-Phenyl-3-hydroxy-7-mercapto-pyrazolo[4,3-d]pyrimidine

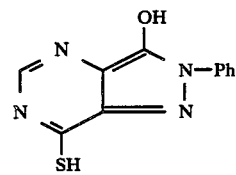

The reaction and treatment were conducted in the same manner as in Example A-20 except that 2-phenyl-3,7-dihydroxy-pyrazolo[4,3-d]pyrimidine was employed, whereby the desired product was obtained.

Yield: 78%.

Melting point: >300° C., yellow powder.

pmr (d$_6$-DMSO) δppm: 7.39–7.91 (m, 6H), 13.67 (br. s, 1H)

EXAMPLE A-22

2-t-Butyl-3-hydroxy-7-mercapto-pyrazolo[4,3-d]pyrimidine

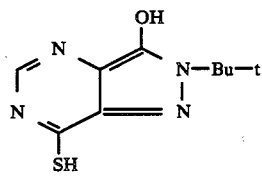

The reaction and treatment were conducted in the same manner as in Example A-20 except that 2-t-butyl-3,7-dihydroxy-pyrazolo[4,3-d]pyrimidine was used, whereby the desired product was obtained.

Yield: 68%.

Melting point: >300° C.

pmr (d$_6$-DMSO) δppm: 1.63 (s, 9H), 7.72 (d, 1H, J=3 Hz), 13.16 (br. s, 1H).

EXAMPLE A-23

2-t-Butyl-3-hydroxy-7-ethoxycarbonylmethylthio-pyrazolo[4,3-d]pyrimidine

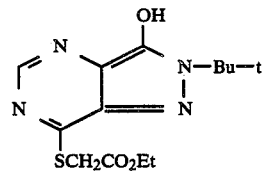

The reaction and treatment were conducted in the same manner as in Example A-6 except that 2-t-butyl-3-hydroxy-7-mercapto-pyrazolo[4,3-d]pyrimidine obtained in Example A-22 was used, whereby the desired compound was obtained.

Yield: 73%.

Melting point: 129°–131° C. (as recrystallized from chloroform-hexane).

pmr (CDCl$_3$) δppm: 1.29 (t, 3H, J=8 Hz), 1.79 (s, 9H), 4.22 (s, 2H), 4.25 (q, 2H, J=8 Hz), 8.47 (s, 1H).

EXAMPLE 1:

2-Methyl-3-n-hexadecyloxy-7-ethoxycarbonylmethylthio-pyrazolo[4,3-d]pyrimidine

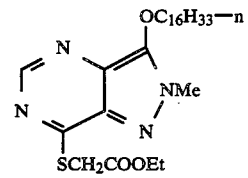

(Synthesis 1)

2.41 g of 2-methyl-3-hydroxy-7-ethoxycarbonyl-methylthio-pyrazolo[4,3-d]pyrimidine obtained in Example A-1 was dissolved in 30 ml of dry dimethylformamide, and 1.73 g of anhydrous potassium carbonate was added. Then, 3.3 g of cetyl bromide was dropwise added at room temperature, and the mixture was heated at 60° C. for 2 hours. After confirming the completion of the reaction by means of thin layer chromatography, water was added while cooling the reaction mixture. Then, the mixture was extracted with chloroform. The chloroform layer was washed with water, and dried over anhydrous magnesium sulfate, and then the solvent was completely distilled off. The remaining solid was purified by silica gel chromatography (developing solution: ethyl acetate/benzene), whereby the desired product was obtained.

Yield: 3.18 g (71.8%).

Melting point: 55.5°–56° C. (as recrystallized from petroleum ether), colorless powder.

pmr (CDCl$_3$) δppm:
0.7–2.0 (m, 34H), 3.96 (s, 3H), 4.14 (s, 2H),
4.22 (q, 2H, J=7 Hz), 4.87 (t, 2H, J=7 Hz), 8.49 (s, 1H).

Mass (m/e): 4.92 (M+).

(Synthesis 2)

The above reaction (Synthesis 1) was duplicated by using n-hexadecyl p-toluenesulfonate instead of cetyl bromide, whereby the yield increased to 4.07 g (92%).

(Synthesis 3)

The above reaction (Synthesis 1) was conducted in the presence of a phase transfer catalyst. Namely, 268 mg of 2-methyl-3-hydroxy-7-ethoxycarbonylmethylthio-pyrazolo[4,3-d]pyrimidine and 475 mg of n-hexadecyl p-toluenesulfonate were dissolved in 10 ml of chloroform, and vigorously stirred at room temperature for 3 days together with 5 ml of an aqueous solution of potassium carbonate (150 mg) and 18-crown-6 (0.2 g). The chloroform layer was dried over anhydrous magnesium sulfate, and evaporated to dryness. The remaining solid was purified by column chromatography to obtain 120 mg of the desired compound.

From the aqueous layer and the chloroform layer, 170 mg of unreacted 2-methyl-3-hydroxy-7-ethoxycarbonyl-methylthio-pyrazolo[4,3-d]pyrimidine was recovered. The yield of the desired compound taking into consideration of the recovery of the starting material, was 72%.

EXAMPLES 2 to 14

The following compounds of Examples 2 to 14 were prepared by the same reaction and treatment as in Example 1 except that instead of n-hexadecyl p-toluenesulfonate used in Synthesis 2 of Example 1, other tosyl compounds or halogen compounds as specified below were employed.

EXAMPLE 2:
2-Methyl-3-n-dodecyloxy-7-ethoxycarbonylmethylthio-pyrazolo[4,3-d]pyrimidine

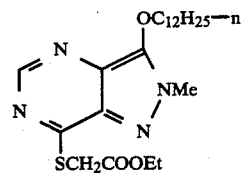

Starting compound: n-dodecyl p-toluenesulfonate.
Yield: 75%.
Melting point: 40.5°–41.5° C. (as recrystallized from hexane).
pmr (CDCl$_3$) δppm: 0.7–2.0 (m, 26H), 3.96 (s, 3H), 4.14 (s, 2H), 4.20 (q, 2H, J=7 Hz), 4.89 (t, 2H, J=6 Hz), 8.49 (s, 1H).
Mass (m/e): 436 (M+).

EXAMPLE 3:
2-Methyl-3-n-tetradecyloxy-7-ethoxycarbonylmethylthio-pyrazolo[

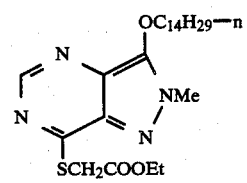

Starting compound: n-tetradecyl p-toluenesulfonate.
Yield: 75%.
Melting point: 47.0°–47.5° C. (as recrystallized from hexane).
pmr (CDCl$_3$) δppm: 0.7–2.0 (m, 30H), 3.96 (s, 3H), 4.14 (s, 2H), 4.24 (q, 2H, J=7 Hz), 4.89 (t, 2H, J=7 Hz), 8.49 (s, 1H).
Mass (m/e): 464 (M+).

EXAMPLE 4:
2-Methyl-3-n-pentadecyloxy-7-ethoxycarbonylmethylthio-pyrazolo[4,3-d]pyrimidine

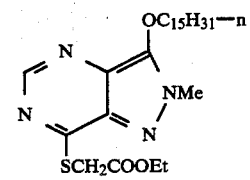

Starting compound: n-pentadecyl p-toluenesulfonate.
Yield: 70%.
Melting point: 37.5°–38.5° C. (as recrystallized from hexane), light yellow crystals.
pmr (CDCl$_3$) δppm: 0.7–2.0 (m, 32H), 3.96 (s, 3H), 4.12 (s, 2H), 4.22 (q, 2H, J=7 Hz), 4.88 (t, 2H, J=6.5 Hz), 8.48 (s, 1H).

EXAMPLE 5:
2-Methyl-3-n-heptadecyloxy-7-ethoxycarbonylmethylthio-pyrazolo[4,3-d]]pyrimidine.

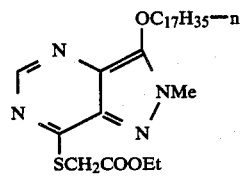

Starting compound: n-heptadecyl p-toluenesulfonate.
Yield: 68%.
Melting point: 42.0°–43.0° C. (as recrystallized from hexane).
pmr (CDCl$_3$) δppm: 0.7–2.0 (m, 36H), 3.95 (s, 3H), 4.13 (s, 2H), 4.21 (q, 2H, J=7.5 Hz), 4.88 (5, 2H, J=6.5 Hz), 8.47 (s, 1H).

EXAMPLE 6:
2-Methyl-3-n-octadecyloxy-7-ethoxycarbonylmethylthio-pyrazolo[4,3-d]pyrimidine.

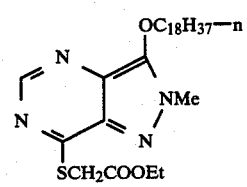

Starting compound: n-octadecyl p-toluenesulfonate.
Yield: 65%.
Melting point: 49.5°–50.5° C. (as recrystallized from hexane).
pmr (CDCl3) δppm: 0.7–2.0 (m, 38H), 3.95 (s, 3H), 4.12 (s, 2H), 4.21 (q, 2H, J=7.5 Hz), 4.87 2H, J=6.5 Hz), 8.47 (s, 1H).

EXAMPLE 7:
2-Methyl-3-n-nonadecyloxy-7-ethoxycarbonylmethylthio-pyrazolo[4,3-d]pyrimidine.

Starting compound: n-nonadecyl p-toluenesulfonate.
Yield: 84%.
Melting point: 48.0°–49.0° C. (as recrystallized from hexane).
pmr (CDCl$_3$) δppm: 0.7–2.0 (m, 40H), 3.95 (s, 3H), 4.14 (s, 2H), 4.22 (q, 2H, J=7.5 Hz), 4.88 (t, 2H, J=6.5 Hz), 8.48 (s, 1H).

EXAMPLE 8:
2-Methyl-3-n-eicosanyloxy-7-ethoxycarbonylmethylthio-pyrazolo[4,3-d]pyrimidine.

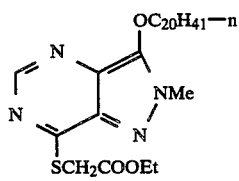

Starting compound: n-eicosyl p-toluenesulfonate.
Yield: 85%.
Melting point: 53.0°–54.0° C. (as recrystallized from hexane).
pmr (CDCl$_3$) δppm: 0.7–2.0 (m, 42H), 3.95 (s, 3H), 4.14 (s, 2H), 4.21 (q, 2H, J=7.5 Hz), 4.88 (t, 2H, J=6.5 Hz), 8.48 (s, 1H).

EXAMPLE 9:
2-Methyl-3-oleyloxy-7-ethoxycarbonylmethylthio-pyrazolo[4,3-d]pyrimidine.

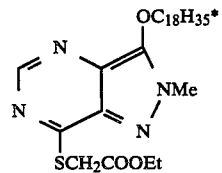

Starting compound: 9-oleyl p-toluenesulfonate.
Yield: 73%, light yellow oily substance.
pmr (CDCl$_3$) δppm: 0.8–2.2 (m, 34H), 3.95 (s, 3H), 4.14 (s, 2H), 4.24 (q, 2H, J=8.0 Hz), 4.88 (t, 2H), 5.35 (m, 2H), 8.45 (s, 1H).
Mass (m/e): 519 (M$^+$+1), 431 (M$^+$—CH$_2$COOEt), 400 (M$^+$SCH$_2$COOEt+1).

EXAMPLE 10:
2-Methyl-3-linoleyloxy-7-ethoxycarbonylmethylthio-pyrazolo[4,3-d]pyrimidine

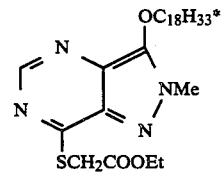

Starting compound: linoleyl p-toluenesulfonate.
Yield: 80%, light yellow oily substance.
Melting point: 22.0°–25.0° C.
pmr (CDCl$_3$) δppm: 0.8–2.2 (m, 28H), 2.6–2.9 (m, 2H), 3.96 (s, 3H), 4.15 (s, 2H), 4.22 (q, 2H, J=7 Hz), 4.89 (t, 2H, J=6.5 Hz), 5.2–5.6 (m, 4H), 8.48 (s, 1H).
Mass (m/e): 516 (M$^+$), 429 (M$^+$—CH$_2$COOEt), 397 (M$^+$—SCH$_2$COOEt), 268 (M$^+$—C$_{18}$H$_{32}$).

EXAMPLE 11:
2-Methyl-3-linolenyloxy-7-ethoxycarbonylmethylthio-pyrazolo[4,3-d]pyrimidine

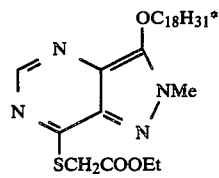

Starting compound: linolenyl p-toluenesulfonate.
Yield: 78%, light yellow oily substance.
pmr (CDCl$_3$) δppm: 0.7–2.3 (m, 22H), 2.6–2.9 (m, 4H), 3.96 (s, 3H), 4.14 (s, 2H), 4.19 (q, 2H, J=7 Hz), 4.89 (t, 2H, J=6 Hz), 5.1–5.6 (m, 6H), 8.48 (s, 1H).
Mass (m/e): 514 (M$^+$), 268 (M$^+$ —C$_{18}$H$_{30}$).

EXAMPLE 12:
2-Methyl-3-(p-methoxybenzyl)oxy-7-ethoxycarbonylmethylthio-pyrazolo[4,3-d]pyrimidine

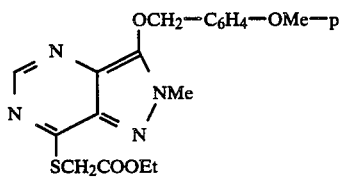

Starting compound: p-methoxybenzyl chloride.
Yield: 34%.
Melting point: 94°–95.5° C. (as crystallized from ether-hexane), colorless powder.
pmr (CDCl$_3$) δppm: 1.28 (t, 3H), 3.80 (s, 3H), 3.87 (s, 3H), 4.14 (s, 2H), 4.22 (q, 2H, J=7 Hz), 5.83 (s, 2H), 6.8–6.9, 7.3–7.4 (m, 2H×2), 8.55 (s, 1H).
Mass (m/e): 388 (M$^+$), 121 (CH$_2$—OMe—C$_6$H$_4$—p$^+$).

EXAMPLE 13:
2-Methyl-3-(2-phenylethyl)oxy-7-ethoxycarbonylmethylthio-pyrazolo[4,3-d]

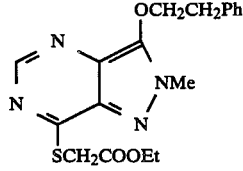

Starting compound: phenethyl bromide.
Yield 68%.
Melting point: 59.5°–60.0° C. (as crystallized from ether-hexane), colorless fluffy crystal
pmr (CDCl$_3$) δppm: 1.27 (t, 3H), 3.16 (t, 2H), 3.83 (s, 3H), 4.13 (s, 2H), 4.21 (q, 2H, J=7 Hz), 5.09 (t, 2H, J=6.8 Hz), 7.27 (m, 5H), 8.50 (s, 1H).
Mass (m/e): 372 (M$^+$), 281 (M$^+$—C$_7$H$_7$), 268 (M$^+$—CH$_2$=CHph).

EXAMPLE 14:
2-Methyl-3-(p-benzyloxybenzyl)oxy-7-ethoxycarbonyl-methylthio-pyrazolo[4,3-d]-pyrimidine

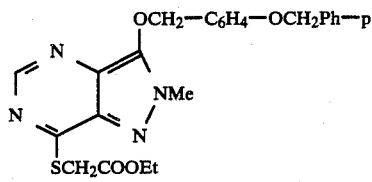

Starting compound: p-benzyloxybenzyl chloride.
Yield: 47%.
Melting point: 81.5°–82.5° C., light yellow powder.
pmr (CDCl$_3$) δppm: 1.27 (t, 3H), 3.86 (s, 3H), 4.13 (s, 2H), 4.22 (q, 2H, J=7 Hz), 5.04 (s, 2H), 5.82 (s, 2H), 6.9–7.0, 7.3–7.5 (m, 9H), 8.55 (s, 1H).
Mass (m/e): 464 (M$^+$), 197 (CH$_2$—C$_6$H$_4$—OCH$_2$-Ph—p$^{30}$) 91 (C$_7$H$_7{}^+$).

EXAMPLES 15 to 26

The following compounds of Examples 15 to 26 were prepared by the same reaction and treatment as in Synthesis 2 of Example 1 except that instead of 2-methyl-3-hydroxy-7-ethoxycarbonylmethylthio-pyrazolo[4,3-d]pyrimidine used in Example 1, other pyrazolo[4,3-d]pyrimidine derivatives as specified below were reacted with n-hexadecyl p-toluene sulfonate.

EXAMPLE 15:
2-Methyl-3-n-hexadecyloxy-7-methoxycarbonylmethylthio-pyrazolo[4,3-d]pyrimidine

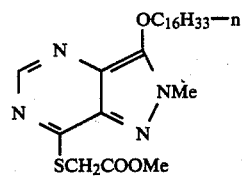

Starting compound: 2-methyl-3-hydroxy-7-methoxycarbonylmethylthio-pyrazolo[4,3-d]pyrimidine.
Yield: 74%.
Melting point: 58.5°–59.5° C. (as recrystallized from hexane), light yellow powder.
pmr (CDCl$_3$) δppm: 0.7–2.0 (m, 34H), 3.76 (s, 3H), 3.95 (s, 3H), 4.16 (s, 2H), 4.88 (t, 2H, J=6.5 Hz), 8.48 (s, 1H).

EXAMPLE 16:
2-Methyl-3-n-hexadecyloxy-7-isopropoxycarbonyl-methylthio-pyrazolo[4,3-d]pyrimidine

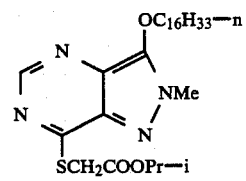

Starting compound: 2-methyl-3-hydroxy-7-isopropoxycarbonylmethylthio-pyrazolo[4,3-d]pyrimidine.

Melting point: 50°–51° C. (as recrystallized from hexane), light yellow powder.
pmr (CDCl$_3$) δppm: 0.7—2.0 (m, 37H), 3.96 (s, 3H), 4.09 (s, 2H), 4.89 (t, 2H, J=6.5 Hz), 5.09 (m, 1H, J=6.5 Hz), 8.46 (s, 1H).

EXAMPLE 17:
2-Methyl-3-n-hexadecyloxy-7-(3-ethoxycarbonyl-propylthio)-pyrazolo[4,3-d]pyrimidine

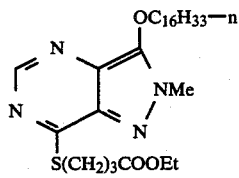

Starting compound: 2-methyl-3-hydroxy-7-(3-ethoxycarbonylpropylthio-pyrazolo[4,3-d]pyrimidine.
Yield: 62%.
Melting point: 38°–39° C. (as recrystallized from petroleum ether), colorless crystals.
pmr (CDCl$_3$) δppm: 0.7–2.0 (m, 34H), 2.10 (q, 2H, J=8 Hz), 2.49 (t, 2H, J=8 Hz), 3.42 (t, 2H, J=8 Hz), 3.95 (s, 3H), 4.12 (q, 2H, J=8 Hz), 4.89 (t, 2H, J=7 Hz), 8.50 (s, 1H).

EXAMPLE 18:
2-Methyl-3-n-hexadecyloxy-7-benzoylmethylthio-pyrazolo[4,3-d]pyrimidine

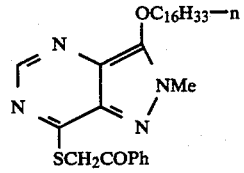

Starting compound: 2-methyl-3-hydroxy-7-benzoyl-methylthio-pyrazolo[4,3-d]pyrimidine.
Yield: 31%.
Melting point: 77°–78° C. (as recrystallized from acetone), light yellow powder.
pmr (CDCl$_3$) δppm: 0.8–2.0 (m, 31H), 3.95 (s, 3H), 4.89 (t+s, 5H, J=7Hz), 7.4 - 8.2 (m, 5H), 8.44 (s, 1H).
Mass (m/e): 524 (M$^+$), 492 (M$^+$—S), 419 (M$^+$—COPh).

EXAMPLE 19:
2-Methyl-3-n-hexadecyloxy-7-benzylthio-pyrazolo[4,3-d]pyrimidine

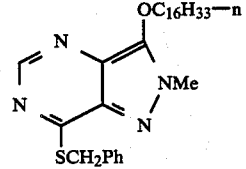

Starting compound: 2-methyl-3-hydroxy-7-benzylthio-pyrazolo[4,3-d]pyrimidine.
Yield: 71%.
Melting point: 63°–64° C. (as recrystallized from hexane).

pmr (CDCl$_3$) δppm: 0.7–2.0 (m, 31H), 3.93 (s, 3H), 4.62 (s, 2H), 4.89 (t, 2H, J=7.4 Hz), 7.2–7.6 (m, 5H), 8.54 (s, 1H).
Mass (m/e): 496 (M$^+$).

EXAMPLE 20:
2-Methyl-3-n-hexadecyloxy-7-(3,4-dichlorophenylmethylthio)-pyrazolo[4,3-d]pyrimidine.

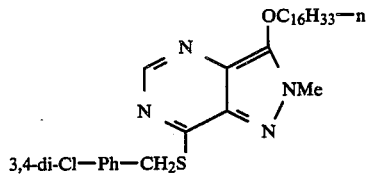

Starting compound: 2-methyl-3-hydroxy-7 (3,4-dichlorophenylmethylthio)-pyrazolo[4,3-d]pyrimidine.
Yield: 74%.
Melting point: 51°–52° C. (as recrystallized from hexane).
pmr (CDCl$_3$) δppm: 0.8–2.0 (m, 31H), 3.97 (s, 3H), 4.54 (s, 2H), 4.89 (t, 2H, J=7.4 Hz), 7.3–7.6 (m, 3H), 8.53 (s, 1H).
Mass (m/e): 564 (M$^+$−1), 405 (M$^+$−CH$_2$−C$_6$H$_3$−Cl$_2$), 340 (M$^+$−C$_{16}$H$_{33}$).

EXAMPLE 21:
2-Methyl-3-n-hexadecyloxy-7-phenethylthio-pyrazolo[d]pyrimidine

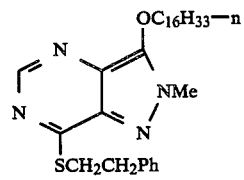

Starting compound: 2-methyl-3-hydroxy-7-phenethylthio-pyrazolo[4,3-d]pyrimidine.
Yield: 75%.
Melting point: 58°–59° C. (as recrystallized from hexane), colorless fluffy crystals.
pmr (CDCl$_3$) δppm: 0.7–2.0 (m, 31H), 3.1 (t, d, 2H, J=8 Hz), 3.6 (t, d, 2H, J=8 Hz), 3.95 (s, 3H), 4.89 (t, 2H, J=6.4 Hz), 7.29 (m, 5H), 8.54 (s, 1H).
Mass (m/e): 510 (M$^+$), 406 (M$^+$−CH$_2$=CHPh), 286 (M$^+$−C$_{16}$H$_{32}$).

EXAMPLE 22:
2-Methyl-3-n-hexadecyloxy-7-allylthio-pyrazolo[[4,3-d]pyrimidine

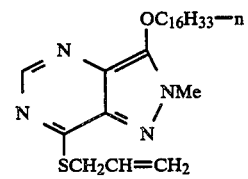

Starting compound: 2-methyl-3-hydroxy-7-allylthiopyrazolo-[4,3-d]pyrimidine.
Yield: 87%.
Melting point: 39°–40° C. (as recrystallized from hexane), colorless powder.

pmr (CDCl$_3$) δppm: 0.7–2.0 (m, 31H), 3.98 (s, 3H), 4.02 (d, 2H, J=6 Hz), 4.89 (t, 2H, J=7 Hz), 5.14 (dd, 1H, J=10Hz, 1 Hz), 5.36 (dd, 1H, J=15 Hz, 1Hz), 5.8–6.2 (m, 1H), 8.51 (s, 1H).
Mass (m/e): 446 (M$^+$), 222 (M$^+$−C$_{16}$H$_{32}$).

EXAMPLE 23:
2-Methyl-3-n-hexadecyloxy-7-n-hexylthiopyrazolo[4,3-d]pyrimidine

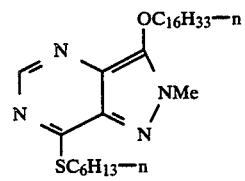

Starting compound: 2-methyl-3-hydroxy-7-n-hexylthiopyrazolo[4,3-d]pyrimidine.
Yield 93%.
Melting point: 39°–45° C. (as recrystallized from petroleum ether).
pmr (CDCl$_3$) δppm: 0.7–2.0 (m, 42H), 3.36 (t, 2H, J=8 Hz), 3.95 (s, 3H), 4.88 (t, 2H, J=7 Hz), 8.50 (s, 1H).
Mass (m/e): 490 (M$^+$), 405 (M$^+$−C$_6$H$_{13}$, 373 (M$^+$−SC$_6$H$_{13}$).

EXAMPLE 24:
2-Methyl-3-n-hexadecyloxy-7-n-hexadecylthio-pyrazolo[4,3-d]pyrimidine

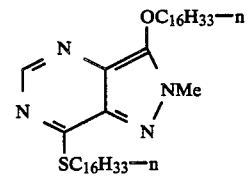

Starting compound: 2-methyl-3-hydroxy-7-n-hexadecylthio-pyrazolo[4,3-d]pyrimidine.
Yield: 77%.
Melting point: 54°–55° C. (as recrystallized from petroleum ether) colorless fluffy crystals.
pmr (CDCl$_3$) δppm: 0.7–2.2 (m, 62H), 3.35 (t, 2H, J=8 Hz), 3.95 (s, 3H), 4.89 (t, 2H, J=8 Hz), 8.50 (s, 1H).
Mass (m/e): 630 (M$^+$), 406 (M$^+$−C$_{16}$H$_{32}$).

EXAMPLE 25:
2-Methyl-3-n-hexadecyloxy-7-[4-(3-methyl-5-oxotetrahydrofuranyl)thio]-pyrazolo[4,3-d]pyrimidine

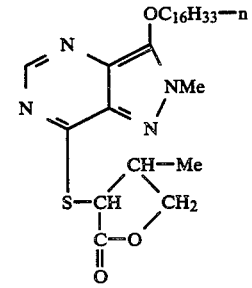

Starting compound: 2-methyl-3-hydroxy-7-[4(3-methyl-5-oxotetrahydrofuranyl)thio]-pyrazolo[4,3-d]pyrimidine Yield: 70%.

Melting point: 59°–61° C., light brown powder.

pmr (CDCl$_3$) δppm: 0.7–2.0 (m, 31H), 1.50, 1.54 (d, 3H, J=7 Hz), 2.0–3.2 (m, 2H), 3.96 (s, 3H), 4.5–5.1 (m, 4H), 8.48, 8.50 (s, 1H) (a mixture of lactone-ring methyl stereoisomers).

Mass (m/e): 504 (M+), 472 (M+—S), 280 (M+—C$_{16}$H$_{32}$).

EXAMPLE 26:

2-Methyl-3-n-hexadecyloxy-7-(1-ethoxycarbonyl-1-methyl-ethylthio)pyrazolo [4,3-d]pyrimidine

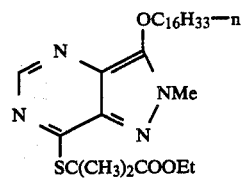

Starting compound: 2-methyl-3-hydroxy-7-(1-ethoxycarbonyl-1-methyl-ethylthio)-pyrazolo [4,3-d]pyrimidine.

Yield: 72%.

Melting point: 40°–42° C., light yellow powder.

pmr (CDCl$_3$) δppm: 0.88 (t, 3H), 1.0–2.0 (m, 28H), 1.15 (t, 3H), 1.79 (s, 6H), 3.94 (s, 3H), 4.18 (q, 2H, J=7 Hz), 4.88 (t, 2H, J=6 Hz), 8.42 (s, 1H).

Mass (m/e): 520 (M+).

EXAMPLES 27 to 30

The following compounds of Examples 27 to 30 were prepared by the same reaction and treatment as in Synthesis 1 of Example 1 except that instead of 2-methyl3-hydroxy-7-ethoxycarbonylmethylthio-pyrazolo[4,3-d]pyrimidine used in Example 1, 2-methyl-3-hydroxy-7-(1-ethoxycarbonyl-1-methyl-ethylthio)-pyrazolo[4,3-d]pyrimidine was reacted with the halogen compounds as specified below.

EXAMPLE 27:

2-Methyl-3-n-octyloxy-7-(1-ethoxycarbonyl1-methyl-ethylthio)-pyrazolo[4,3-d]pyrimidine

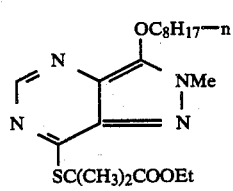

Starting compound: n-octyl bromide.

Yield: 54%.

Melting point: 30.5°–31° C., light yellow powder.

pmr (CDCl$_3$) δppm: 0.88 (t, 3H), 1.0–2.0 (m, 12H), 1.15 (t, 3H, J=7 Hz), 1.77 (s, 6H), 3.92 (s, 3H), 4.15 (q, 2H, J=7 Hz), 4.85 (t, 2H, J=6 Hz), 8.38 (s, 1H).

Mass (m/e): 408 (Me+), 296 (M+ —C$_8$H$_{16}$), 182 (296 —CH$_2$=C(CH$_3$)COOEt).

EXAMPLE 28:

2-Methyl-3-n-dodecyloxy-7-(1-ethoxycarbonyl-1-methyl-ethylthio)-pyrazolo[4,3-d]pyrimidine

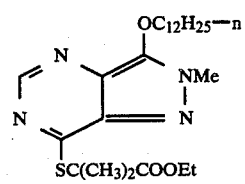

Starting compound: n-dodecyl bromide.

Melting point: 29°–30° C., light yellow solid.

pmr (CDCl$_3$) δpm: 0.88 (t, 3H), 1.0–2.0 (m, 20H), 1.15 (t, 3H), 1.79 (s, 6H), 3.94 (s, 3H), 4.15 (q, 2H, J=6 Hz), 4.88 (t, 2H, J=6 Hz), 8.42 (s, 1H).

EXAMPLE 29:

2-Methyl-3-n-eicosyloxy-7-(1-ethoxycarbonyl-1-methyl-ethylthio)-pyrazolo[4,3-d]pyrimidine

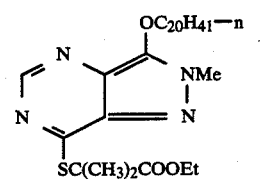

Starting compound: n-eicosyl bromide.

Yield: 71%.

Melting point: 3.9°–40.5° C. (as recrystallized from petroleum ether), colorless powder.

pmr (CDCl$_3$) δppm: 0.88 (t, 3H), 1.0–2.0 (m, 36H), 1.15 (t, 3H), 1.79 (s, 6H), 3.94 (s, 3H), 4.15 (q, 2H, J=6 Hz), 4.88 (t, 2H, J=6 Hz), 8.42 (s, 1H).

Mass (m/e): 576 (M+).

EXAMPLE 30:

2-Methyl-3-(2-hydroxyethyloxy)-7-(1-ethoxycarbonyl-1-methyl-ethylthio) pyrazolo[4,3-d]pyrimidine

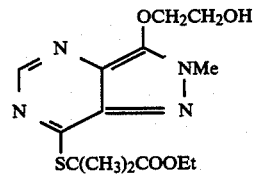

Starting compound: epichlorohydrin.

Yield: 58%.

Melting point: 91.5°–92° C., yellowish orange powder.

pmr (CDCl$_3$) δppm: 1.15 (t, 3H), 1.79 (s, 6H), 3.99 (s, 3H), 4.0–4.2 (m, 2H), 4.15 (q, 2H, J=7 Hz), 4.80–4.95 (m, 2H), 8.41 (s, 1H).

Mass (m/e): 340 (M+), 296 (M+—CH$_2$=CHOH), 225 (M+—C(CH$_3$)$_2$COOEt).

EXAMPLE 31:
2-Phenyl-3-n-heptyloxy-7-ethoxycarbonylmethylthio-pyrazolo[4,3-d]pyrimidine

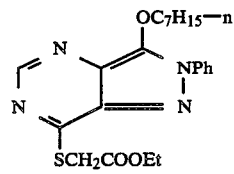

1 g of 2-phenyl-3-hydroxy-7-ethoxycarbonylmethylthio-pyrazolo[4,3-d]pyrimidine was dissolved in 10 ml of DMF, and 0.5 g of anhydrous potassium carbonate and 0.65 g of bromoheptane were added thereto. The mixture was stirred at room temperature for 48 hours. Then, after confirming the completion of the reaction by means of TLC, an aqueous hydrochloric acid solution was added. The reaction mixture was extracted with chloroform. The chloroform layer was washed with an aqueous sodium chloride solution, and dried over anhydrous magnesium sulfate, and then chloroform was distilled off. The residue was purified by silica gel chromatography (60% chloroform-hexane), whereby the desired product was obtained.

Oily substance (solidified when left to stand still), yield: 0.39 g (30%).

pmr (CDCl$_3$) δppm: 0.87 (t, 3H), 0.7-2.0 (m, 13H), 4.16 (s, 2H), 4.24 (q, 2H, J=7.3 Hz), 4.96 (t, 2H, J=6.4 Hz), 7.40-7.90 (m, 5H), 8.53 (s, 1H).

EXAMPLE 32:
2-Phenyl-3-n-dodecyloxy-7-(1-ethoxycarbonyl-1-methylethylthio)-pyrazolo[4,3-d]pyrimidine

1 g of 2-phenyl-3-hydroxy-7-(1-ethoxycarbonyl-1-methyl-ethylthio)-pyrazolo[4,3-d]pyrimidine and 0.84 g of n-dodecyl bromide were reacted and treated in the same manner as in Example 31 to obtain the desired product.

Yield: 30%, oily substance.

pmr (CDCl$_3$) δppm: 0.88 (t, 3H), 0.7-2.0 (m, 23H), 1.80 (s, 6H), 4.19 (q, 2H, J=7.3 Hz), 4.14 (t, 2H, J=6.3 Hz), 7.44-7.89 (m, 5H), 8.46 (s, 1H).

EXAMPLE 33:
2-Methyl-3-n-hexadecyloxy-7-n-butoxycarbonylmethylthio-pyrazolo[4,3-d]pyrimidine

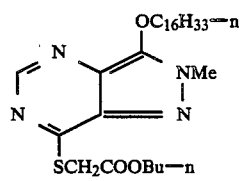

2-Methyl-3-hydroxy-7-n-butoxycarbonylmethylthiopyrazolo[4,3-d]pyrimidine and n-hexadecyl p-toluenesulfonate were reacted and treated in the same manner as in Synthesis 2 of Example 1 to obtain the desired compound.

Yield: 75%.

Melting point: 64.0°-67.0° C. (as recrystallized from hexane), light brown powder.

pmr (CDCl$_3$) δppm: 0.7-2.0 (m, 38H), 3.96 (s, 3H), 4.13 (s, 2H), 4.15 (q, 2H, J=3 Hz), 4.88 (5, 2H, J=7.5 Hz), 8.48 (s, 1H).

Mass (m/e): 520 (M+), 296 (M+—C$_{16}$H$_{32}$), 195 (296 —CO$_2$C$_4$H$_9$).

EXAMPLES 34 to 45

The following compounds of Examples 34 to 45 were prepared by the same reaction and treatment as in Synthesis 2 of Example 1 except that instead of n-hexadecyl p-toluenesulfonate used in Synthesis 2 of Example 1, other tosyl compounds were employed, and instead of dimethylformamide, dimethylacetamide was employed.

EXAMPLE 34:
2-Methyl-3-(4-cyclohexyl-cyclohexyloxy)-7-ethoxycarbonylmethylthio-pyrazolo[4,3-d]pyrimidine

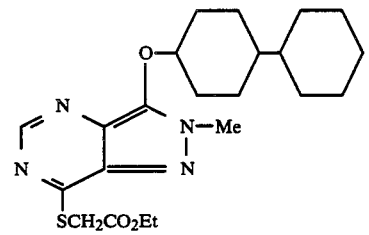

Starting compound: 4-cyclohexyl-cyclohexyl p-toluenesulfonate.

Yield: 27% (Two types of isomers (1) and (2) were isolated by the recrystallization from hexane.)

(1) white plate-like crystals 8% (mp 120°-121° C.)
(2) white needle-like crystals 19% (mp 75°-76° C.)

pmr (CDCl$_3$) δppm: Signals common to (1) and (2): 0.8-2.5 (m, 23H), 3.99 (s, 3H), 4.14 (s. 2H), 4.23 (q, 2H, J=7 Hz), 8.49 (s, 1H).

Signal specific to (1): 5.75 (br. s., 1H).
Signal specific to (2): 5.1-5.5 (m, 1H).
Mass (m/e): 432 (M+).

EXAMPLE 35:
2-Methyl-3-(4-methylcyclohexyloxy)-7-ethoxycarbonylmethylthio-pyrazolo[4,3-d]pyrimidine

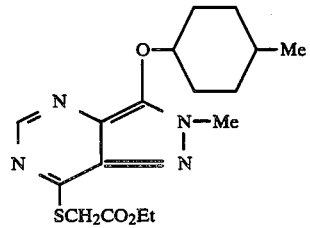

Starting compound: 4-methylcyclohexyl p-toluenesulfonate.

Yield: 44.2%, light yellow oily substance.

pmr (CDCl$_3$) δppm: 0.8-2.5 (m, 15H), 3.99 (s, 3H), 4.14 (s, 2H), 4.22 (q, 2H, J=7 Hz), 5.7-5.8 (m, 1H), 8.49 (s, 1H).

Mass (m/e): 365 (M++1).

EXAMPLE 36:
2-Methyl-3-(2-benzyloxyethoxy)-7-ethoxycarbonyl-methylthio-pyrazolo[4,3-d]pyrimidine

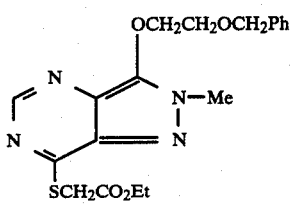

Starting compound: 2-benzyloxyethyl p-toluenesulfonate.

Yield: 72.0%, yellow oily substance.

pmr (CDCl$_3$) δppm: 1.27 (t, 3H, J=7 Hz), 3.86 (m, 2H), 3.96 (s, 3H), 4.13 (s, 2H), 4.22 (q, 2H, J=7 Hz), 4.57 (s, 2H), 5.04 (m, 2H), 7.30 (s, 5H), 8.47 (s, 1H).

Mass (m/e): 402 (M+).

EXAMPLE 37:
2-Methyl-3-[2-(4-ethylbenzyloxy)ethoxy]7-ethoxycarbonylmethylthio-pyrazolo[4,3-d]pyrimidine

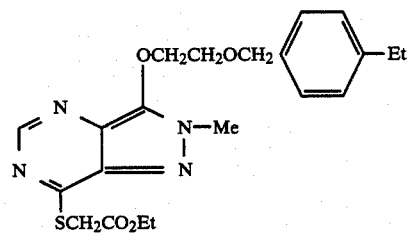

Starting compound: 2-(4-ethylbenzyloxy)ethyl p-toluenesulfonate.

Yield: 34.6%.

Melting point: 51.0°–54.0° C. (as recrystallized from hexane), white crystals.

pmr (CDCl$_3$) δppm: 1.0–2.0 (m, 6H), 2.64 (q, 2H, J=7 Hz), 3.8–4.0 (m, 2H), 3.97 (s, 3H), 4.14 (s, 2H), 4.23 (q, 2H, J=7 Hz), 4.55 (s, 2H), 5.0–5.2 (m, 2H), 7.19 (s, 4H), 8.47 (s, 1H).

Mass (m/e): 430 (M+).

EXAMPLE 38:
2-Methyl-3-[2-(4-t-butylbenzyloxy)ethoxy]-7-ethoxycarbonylmethylthio-pyrazolo[4,3-d]pyrimidine

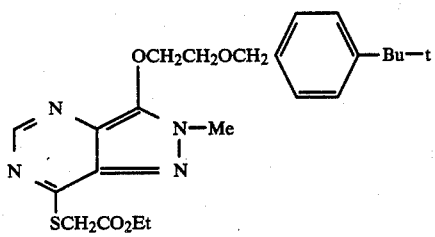

Starting compound: 4-t-butylbenzyloxyethyl p-toluene sulfonate.

Yield: 71.4%, yellow oily substance.

pmr (CDCl$_3$) δppm: 1.0–2.0 (m, 12H), 3.89 (m, 2H), 3.97 (s, 3H), 4.13 (s, 2H), 4.22 (q, 2H, J=7 Hz), 4.55 (s, 2H), 5.05 (m, 2H), 7.32 (m, 4H), 8.47 (s, 1H).

Mass (m/e): 458 (M+).

EXAMPLE 39:
2-Methyl-3-(3,6-dioxadecyloxy)-7-ethoxycarbonyl-methylthio-pyrazolo[4,3-d]pyrimidine

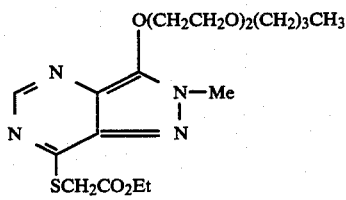

Starting compound 3,6-dioxadecyl p-toluenesulfonate.

Yield: 48.6%, light yellow oily substance.

pmr (CDCl$_3$) δppm: 0.8–2.0 (m, 10H), 3.3–3.9 (m, 8H), 3.99 (s, 3H), 4.15 (s, 2H), 4.22 (q, 2H, J=7 Hz), 5.02 (m, 2H), 8.47 (s, 1H).

Mass (m/e): 412 (M+).

EXAMPLE 40:
2-Methyl-3-(3,7,11,15-tetramethylhexadecyloxy)-7-ethoxycarbonylmethylthio-pyrazolo[4,3-d]pyrimidine

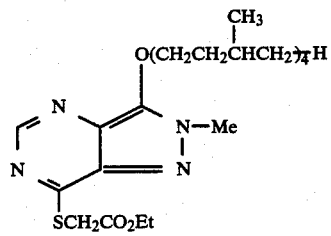

Starting comound: 3,7,11,15-tetramethyl-hexadecyl p-toluenesulfonate.

Yield: 70.8%, light yellow oily substance.

pmr (CDCl$_3$) δppm: 0.7–2.7 (m, 42H), 3.95 (s, 3H), 4.13 (s, 2H), 4.22 (q, 2H, J=7 Hz), 4.95 (t, 2H), 8.47 (s, 1H).

Mass (m/e): 548 (M+), 461 (M+—CH$_2$CO$_2$Et), 268.

EXAMPLE 41:
2-Methyl-3-(3,7,11-trimethyl-dodecyloxy)-7-ethoxycarbonylmethylthio-pyrazolo[4,3-d]pyrimidine

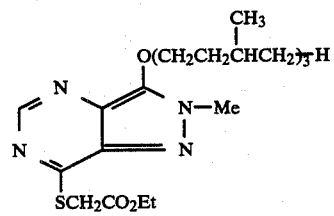

Starting compound: 3,7,11-trimethyl-dodecyl p-toluene sulfonate.

Yield: 73.5%, yellow oily substance.

pmr (CDCl$_3$) δppm: 0.8–2.0 (m, 32H), 3.96 (s, 3H), 4.14 (s, 2H), 4.23 (q, 2H, J=7 Hz), 4.95 (t, 2H, J=7 Hz), 8.49 (s, 1H).

Mass (m/e): 478 (M+), 268 (M+—C$_{15}$H$_{30}$).

EXAMPLE 42:
2-Methyl-3-n-octyloxy-7-ethoxycarbonylmethylthio-pyrazolo[4,3-d]pyrimidine

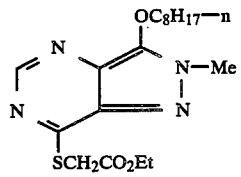

Starting compound: n-octyl p-toluenesulfonate.
Yield: 29%.
Melting point: 29°–31° C. (as recrystallized from hexane), colorless fluffy crystals.
pmr (CDCl$_3$) δppm: 0.8–2.0 (m, 18H), 3.96 (s, 3H), 4.14 (s, 2H), 4.22 (q, 2H, J=7 Hz), 4.89 (t, 2H, J=7 Hz), 8.49 (s, 1H).
Mass (m/e): 380 (M+), 268 (M+—C$_8$H$_{16}$).

EXAMPLE 43:
2-Methyl-3-(1-methylpentadecyloxy)-7-ethoxycarbonylmethylthio-pyrazolo[4,3-d]pyrimidine

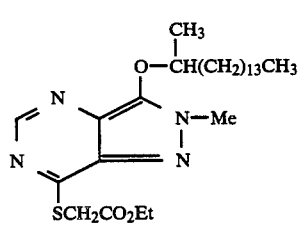

Starting compound: 1-methylpentadecyl p-toluenesulfonate.
Yield: 40%.
Melting point: 39.5°–40.0° C. (as recrystallized from hexane), white crystals.
pmr (CDCl$_3$) δppm: 0.8–2.0 (m, 35H), 3.95 (s, 3H), 4.14 (s, 2H), 4.14 (s, 2H), 4.23 (q, 2H, J=7 Hz), 5.60 (m, 1H), 8.50 (s, 1H).
Mass (m/e): 492 (M+).

EXAMPLE 44:
2-Methyl-3-(9-octadecynyloxy)-7-ethoxycarbonylmethylthio-pyrazolo[4,3-d]pyrimidine

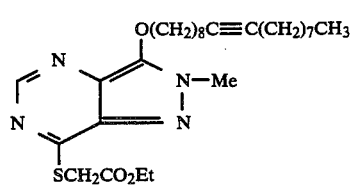

Starting compound: 9-octadecynyl p-toluenesulfonate.
Yield: 51.5%.
Melting point: 25°–26° C., (as recrystallized from methanol), colorless fluffy crystals.
pmr (CDCl$_3$) δppm: 0.87 (t, 3H, J=7 Hz), 1.1–2.3 (m, 28H), 3.96 (s, 3H), 4.14 (s, 2H), 4.22 (q, 2H, J=7 Hz), 4.89 (t, 2H, J=7 Hz), 8.49 (s, 1H).
Mass (m/e): 516 (M+), 471 (M+—OEt), 429 (M+—CH$_2$CO$_2$Et), 397 (M+—SCH$_2$CO$_2$Et), 268.

EXAMPLE 45:
2-methyl-3-(9-decenyloxy)-7-ethoxycarbonylmethylthio-pyrazolo[4,3-d]pyrimidine

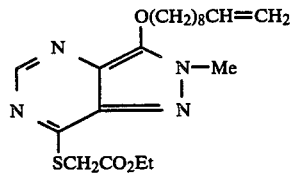

Starting compound: 9-decenyl p-toluenesulfonate.
Yield: 89.7%, light brown oily substance.
pmr (CDCl$_3$) δppm: 1.1–2.2 (m, 17H), 3.96 (s, 3H), 4.14 (s, 2H), 4.22 (q, 2H, J=7 Hz), 4.89 (5, 2H, J=6 Hz), 4.9–5.1 (m, 1H), 5.2–6.0 (m, 2H), 8.48 (s, 1H).
Mass (m/e): 406 (M+), 361 (M+—OC$_2$H$_5$), 268 (M+—decenyl).

EXAMPLE 46:
2-Methyl-3-(4-oxo-pentyloxy)-7-ethoxycarbonymethylthio-pyrazolo[4,3-d]pyrimidine

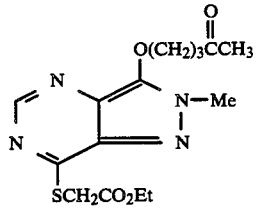

2-Methyl-3-hydroxy-7-ethoxycarbonylmethylthio-pyrazolo[4,3-d]pyrimidine and 4-oxo-pentylchloride were reacted and treated in the same manner as in Synthesis 1 of Example 1 to obtain the desired compound.
Yield: 36.0%.
Melting point: 51°–53° C., light brown powder.
pmr (CDCl$_3$) δppm : 1.28 (t, 3H), 2.19 (s, 3H), 2.0–2.4 (m, 2H), 2.68 (t, 2H, J=7 Hz), 3.96 (s, 3H), 4.13 (s, 2H), 4.22 (q, 2H, J=7 Hz), 4.90 (t, 2H, J=6 Hz), 8.47 (s, 1H).
Mass (m/e): 268 (M+—(CH$_2$)$_3$COCH$_3$+1), 85 ((CH$_2$)$_3$COCH$_3$).

EXAMPLES 47 to 53

The following compounds of Examples 47 to 53 were prepared by the same reaction and treatment as in Example 31 except that 2-phenyl-3-hydroxy-7-ethoxycarbonylmethylthio-pyrazolo[4,3-d]pyrimidine was reacted by using various tosylates instead of bromoheptane and dimethylacetamide instead of DMF as the solvent.

EXAMPLE 47:
2-Phenyl-3-(3-hexenyloxy)-7-ethoxycarbonylmethylthio-pyrazolo[4,3-d]pyrimidine

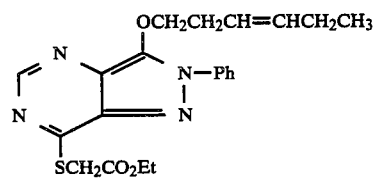

Starting compound: 3-hexenyl p-toluenesulfonate.

Yield: 55.6%, dark red oily substance.

pmr (CDCl$_3$) δppm: 0.92 (t, 3H, J=7 Hz), 1.29 (t, 3H, J=7 Hz), 1.87-2.19 (m, 2H), 2.62 (q, 2H, J=6 Hz), 4.16 (s, 2H), 4.24 (q, 2H, 7 Hz), 4.98 (t, 2H, J=7 Hz), 5.23-5.68 (m, 2H), 7.36-7.91 (m, 5H), 8.52 (s, 1H).

Mass (m/e): 412 (M+).

EXAMPLE 48:
2-Phenyl-3-[2-(4-t-butylbenzyloxy)ethyloxy]-7-ethoxycarbonylmethylthio-pyrazolo[4,3-d]pyrimidine Starting compound: 2-(4-t-butylbenzyloxy)ethyl p-toluenesulfonate.

Yield: 45.2%, brown oily substance.

pmr (CDCl$_3$) δppm: 1.29 (t, 3H, J=7 Hz), 1.31 (s, 9H), 3.86 (m, 2H), 4.15 (s, 2H), 4.24 (q, 2H, J=7 Hz), 4.51 (s, 2H), 5.16 (m, 2H), 7.11-7.95 (m, 5H), 8.51 (s, 1H).

Mass (m/e): 520 (M+).

EXAMPLE 49:
2-Phenyl-3-(3-thia-heptyloxy)-7-ethoxycarbonylmethylthio-pyrazolo[4,3-d]pyrimidine Starting compound: 3-thia-heptyl p-toluenesulfonate.

Yield: 43.4%, brown oily substance.

pmr (CDCl$_3$) δppm: 0.89 (t, 3H, J=7 Hz), 1.20-1.66 (m, 4H), 1.29 (t, 3H, J=7 Hz), 2.58 (t, 2H, J=7 Hz), 2.98 (t, 2H, J=7 Hz), 4.16 (s, 2H), 4.24 (q, 2H, J=7 Hz), 5.10 (t, 2H, J=7 Hz), 7.40-7.94 (m, 5H), 8.51 (s, 1H).

Mass (m/e): 446 (M+).

EXAMPLE 50:
2-Phenyl-3-oleyloxy-7-ethoxycarbonylmethylthio-pyrazolo[4,3-d]pyrimidine

*C$_{18}$H$_{35}$: oleyl

Starting compound: oleyl p-toluenesulfonate.

Yield: 48.9%, brown oily substance.

pmr (CDCl$_3$) δppm: 0.31-2.19 (m, 34H), 4.16 (s, 2H), 4.24 (q, 2H, 7 Hz), 4.94 (t, 2H, 7 Hz), 5.26-5.37 (m, 2H), 7.44-7.89 (m, 5H), 8.52 (s, 1H).

Mass (m/e): 579 (M+−1).

EXAMPLE 51:
2-Phenyl-3-(9-decenyloxy)-7-ethoxycarbonylmethylthio-pyrazolo[4,3-d]pyrimidine Starting compound: 9-decenyl p-toluenesulfonate.

Yield: 35.9%, brown oily substance.

pmr (CDCl$_3$) δppm: 1.29 (t, 3H, 7 Hz), 1.21-2.21 (m, 16H), 4.16 (s, 2H), 4.24 (q, 2H, 7 Hz), 4.85-5.10 (m, 4H), 5.59-5.96 (m, 1H), 7.44-7.90 (m, 5H), 8.53 (s, 1H).

Mass (m/e): 468 (M+).

EXAMPLE 52:
2-Phenyl-3-n-hexadecyloxy-7-ethoxycarbonylmethylthio-pyrazolo[4,3-d]pyrimidine Starting compound: n-hexadecyl p-toluenesulfonate.

Yield: 27.6%.

Melting point: 50°-51° C. (as recrystallized from ethanol).

pmr (CDCl$_3$) δppm: 0.81-1.90 (m, 34H), 4.16 (s, 2H), 4.24 (q, 2H, J=7 Hz), 4.95 (t, 2H, 7 Hz), 7.45-7.89 (m, 5H), 8.53 (s, 1H).

EXAMPLE 53:
2-Phenyl-3-(3-heptenyloxy)-7-ethoxycarbonylmethylthio-pyrazolo[4,3-d]pyrimidine Starting compound: 3-heptenyl p-toluenesulfonate.

Yield: 34.4%, brown oily substance.

pmr (CDCl$_3$) δppm: 0.85 (t, 3H, J=7 Hz), 1.29 (t, 3H, J=7 Hz), 1.12-2.65 (m, 6H), 4.16 (s, 2H), 4.24 (q, 2H, J=7 Hz), 4.98 (t, 2H, J=7 Hz), 5.34-5.58 (m, 2H), 7.43-7.90 (m, 5H), 8.52 (s, 1H).

Mass (m/e): 426 (M+).

EXAMPLE 54:
2-Methyl-3-linoleyloxy-7-methoxycarbonylmethylthio-pyrazolo[4,3-d]pyrimidine

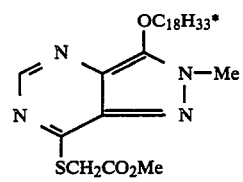

*C$_{18}$H$_{33}$: linoleyl 1.0 g of 2-methyl-3-hydroxy-7-methoxycarbonyl-methylthio-pyrazolo[4,3-d]pyrimidine was dissolved in 10 ml of dry dimethylacetamide, and then 0.54 g of anhydrous potassium carbonate was added thereto. Then, 1.82 g of linoleyl p-tolunesulfonate was dropwise added thereto at room temperature, and then the mixture was heated at 60° C. for 2.5 hours. After confirming the completion of the reaction by means of thin layer chromatography, the reaction mixture was treated in the same manner as in Synthesis 1 of Example 1, whereby the desired product was obtained.

Yield: 57.1%, light yellow oily substance.

pmr (CDCl$_3$) δppm: 0.8–3.0 (m, 31H), 3.76 (s, 3H), 3.96 (s, 3H), 4.16 (s, 2H), 5.36 (m, 2H), 8.49 (s, 1H).

EXAMPLES 55 to 64

The following compounds of Examples 55 to 64 were prepared by the same reaction and treatment as in Example 54 except that instead of 2-methyl-3-hydroxy-7-methoxycarbonylmethylthio-pyrazolo[4,3-d]pyrimidine used in Example 54, other 3-hydroxy-pyrazolo[4,3-d]pyrimidine was used.

EXAMPLE 55:
2-Methyl-3-linoleyloxy-7-n-hexylthio-pyrazolo[4,3-d]pyrimidine

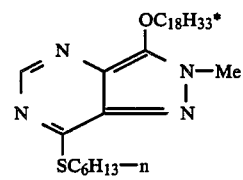

°C$_{18}$H$_{33}$: linoleyl

Starting compound: 2-methyl-3-hydroxy-7-n-hexylthio-pyrazolo[4,3-d]pyrimidine (Compound of Example A-16).

Yield: 84.6%, light brown oily substance.

pmr (CDCl$_3$) δppm: 0.7–2.2 (m, 36H), 2.7–2.9 (m, 2H), 3.36 (t, 2H, J=7 Hz), 3.95 (s, 3H), 4.89 (t, 2H, J=6 Hz), 5.2–5.5 (m, 4H), 8.51 (s, 1H).

Mass (m/e): 514 (M+), 429 (M+—C$_6$H$_{13}$), 397 (M+—SC$_6$H$_{13}$), 266 (M+—C$_{18}$H$_{32}$), 182.

EXAMPLE 56:
2-Methyl-3-linoleyloxy-7-n-butoxycarbonylmethylthio-pyrazolo[4,3-d]pyrimidine

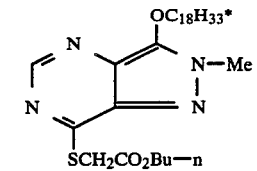

*C$_{18}$H$_{33}$: linoleyl

Starting compound: 2-methyl-3-hydroxy-7-n-butoxycarbonylmethylthio-pyrazolo[4,3-d]pyrimidine.

Yield: 78.3%, yellow oily substance.

pmr (CDCl$_3$) δppm: 0.9 (2×t, 6H), 1.1–2.9 (m, 28H), 3.96 (s, 3H), 4.13 (s, 2H), 4.15 (q, 2H, J=7 Hz), 4.89 (t, J=6 Hz), 5.2–5.5 (m, 4H), 8.48 (s, 1). Mass (m/e): 544 (M+), 429 (M+—CH$_2$CO$_2$Bu-n), 296 (M+C$_{18}$H$_{33}$), 183 (296 —CH$_2$CO$_2$Bu-n).

EXAMPLE 57:
2-Methyl-3-linoleyloxy-7-cyanomethylthio-pyrazolo[4,3-d]pyrimidine

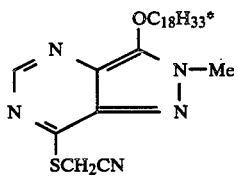

*C$_{18}$H$_{33}$: linoleyl

Starting compound: 2-methyl-3-hydroxy-7-cyanomethylthio-pyrazolo[4,3-d]pyrimidine (Compound of Example A-17).

Yield: 52.1%, brown oily substance.

pmr (CDCl$_3$) δppm: 0.7–2.3 (m, 25H), 2.6–2.9 (m, 2H), 3.97 (s, 3H), 4.16 (s, 2H), 4.91 (t, 2H, J=6 Hz), 5.2–5.5 (m, 4H), 8.59 (s, 1H).

Mass (m/e): 470 (M++1), 429 (M+—CH$_2$CN), 397 (M+—SCH$_2$CN), 221 (M+—C$_{18}$H$_{32}$).

EXAMPLE 58:
2-Methyl-3-linoleyloxy-7-(1-ethoxycarbonylethylthio)-pyrazolo[4,3-d]pyrimidine

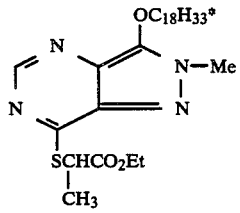

*C$_{18}$H$_{33}$: linoleyl

Starting compound: 2-methyl-3-hydroxy-7-(1-ethoxycarbonylethylthio)pyrazolo[4,3-d]pyrimidine (Compound of Example A-18).

Yield: 82.1%, light yellow oily substance.

pmr (CDCl$_3$) δppm: 0.7–2.2 (m, 28H), 1.69 (d, 3H, J=7 Hz), 2.6–2.9 (m, 2H), 3.95 (s, 3H), 4.21 (q, 2H, J=7 Hz), 4.7–5.0 (t+q, 2H+1H), 5.2–5.5 (m, 4H), 8.48 (s, 1H).

Mass (m/e): 530 (M+), 429 (M+—CHCH$_3$CO$_2$Et), 397 (M+—SCHCH$_3$CO$_2$Et), 282 (M+—C$_{18}$H$_{32}$).

EXAMPLE 59:
2-Methyl-3-linoleyloxy-7-[3-(ethoxycarbonyl)propyl-thio]-pyrazolo[4,3-d]pyrimidine

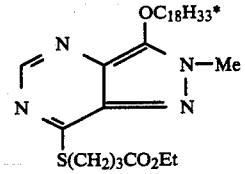

*$C_{18}H_{33}$: linoleyl

Starting compound: 2-methyl-3-hydroxy-7-[3-(ethoxycarbonyl)propylthio]-pyrazolo[4,3-d]pyrimidine.
Yield: 85.5%, light yellow oily substance.
pmr (CDCl$_3$) δppm: 0.7–2.9 (m, 34H), 3.42 (t, 2H, J=7 Hz), 3.95 (s, 3H), 4.14 (q, 2H, J=7 Hz), 4.89 (t, 2H, J=6 Hz), 5.2–5.5 (m, 4H), 8.49 (s, 1H).
Mass (m/e): 544 (M$^+$), 429 (M$^+$—(CH$_2$)$_3$CO$_2$Et), 397 (429-S), 296 (M$^+$—C$_{18}$H$_{32}$), 182, 115 ((CH$_2$)$_3$CO$_2$Et).

EXAMPLE 60:
2-Methyl-3-linoleyloxy-7-[4-(ethoxycarbonyl)butylthio]-pyrazolo[4,3-d]pyrimidine

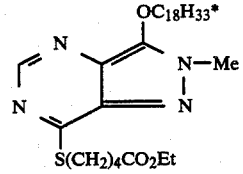

*$C_{18}H_{33}$: linoleyl

Starting compound: 2-methyl-3-hydroxy-7-[4-(ethoxycarbonyl)butylthio]-pyrazolo[4,3-d]pyrimidine.
Yield: 74.8%, light yellow oily substance.
pmr (CDCl$_3$) δppm: 0.7–2.9 (m, 36H), 3.2–3.5 (m, 2H), 3.95 (s, 3H), 4.12 (q, 2H, J=7 Hz), 4.89 (t, 2H, J=6 Hz), 5.2–5.5 (m, 4H), 8.50 (s, 1H).
Mass (m/e): 558 (M$^+$), 429 (M$^+$—(CH$_2$)$_4$CO$_2$Et), 397 (429-S), 310 (M$^+$—C$_{18}$H$_{32}$), 182, 129.

EXAMPLE 61:
2-Methyl-3-linoleyloxy-7-(10-ethoxycarbonyl-n-octyl-thio)-pyrazolo[4,3-d]pyrimidine

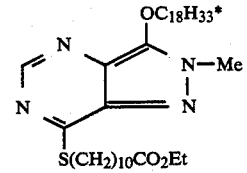

*$C_{18}H_{33}$: linoleyl

Starting compound: 2-methyl-3-hydroxy-7-[10(ethoxycarbonyl)-n-octylthio]pyrazolo[4,3-d]pyrimidine.
Yield: 61.3%, light brown oily substance.
pmr (CDCl$_3$) δppm: 0.7–2.9 (m, 48H), 3.35 (t, 2H, J=7Hz), 3.95 (s, 3H), 4.12 (q, 2H, J=7 Hz), 4.89 (t, 2H, J=6 Hz), 5.2–5.5 (m, 4H), 8.51 (s, 1H).
Mass (m/e): 642 (M$^+$), 597 (M$^+$—OC$_2$H$_5$), 429 (M$^+$—(CH$_2$)$_{10}$CO$_2$Et), 397 (429-S), 394 (M$^+$—C$_{18}$H$_{32}$), 182.

EXAMPLE 62:
2-Methyl-linoleyloxy-7-benzylthio-pyrazolo[4,3-d]pyrimidine

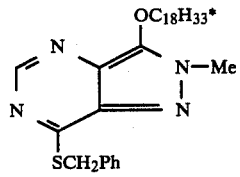

*$C_{18}H_{33}$: linoleyl

Starting compound: 2-methyl-3-hydroxy-7-benzylthio-pyrazolo[4,3-d]pyrimidine.
Yield: 83.1%, light yellow oily substance.
pmr (CDCl$_3$) δppm: 0.7–2.9 (m, 27H), 3.93 (s, 3H), 4.61 (s, 2H), 4.88 (t, 2H, J=6 Hz), 5.2–5.5 (m, 4H), 7.2–7.6 (m, 5H), 8.54 (s, 1H).
Mass (m/e): 520 (M$^+$), 429 (M$^+$—C$_7$H$_7$$^+$), 397 (429-S), 272 (M$^+$—C$_{18}$H$_{32}$), 91.

EXAMPLE 63:
2-Methyl-3-linoleyloxy-7-(1-ethoxycarbonyl-2-methyl-propylthio)pyrazolo[4,3-d]pyrimidine

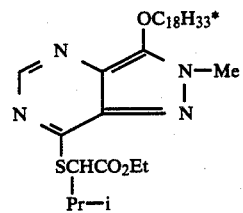

*$C_{18}H_{33}$: linoleyl

Starting compound: 2-methyl-3-hydroxy-7-(1-ethoxycarbonyl-2-methylpropylthio)pyrazolo[4,3-d]pyrimidine.
Yield: 90%, light yellow oily substance.
pmr (CDCl$_3$) δppm: 0.7–2.9 (m, 37H), 3.96 (s, 3H), 4.21 (q, 2H, J=7 Hz), 4.87 (d, 1H, J=5 Hz), 4.89 (t, 2H, J=7 Hz), 5.2–5.5 (m, 4H), 8.47(s, 1H).

Mass (m/e): 558 (M$^+$), 429 (M$^+$—CHCO$_2$Et), 397 (429-S),
                                          |
                182                      Pr—i

EXAMPLE 64:
2-Methyl-3-linoleyloxy-7-allylthio-pyrazolo[4,3-d]pyrimidine

*$C_{18}H_{33}$: linoleyl

Starting compound: 2-methyl-3-hydroxy-7-allylthio-pyrazolo[4,3-d]pyrimidine.
Yield: 85.8%, light yellow oily substance.
pmr (CDCl$_3$) δppm: 0.9 (t, 3H), 1.1–2.9 (m, 24H), 3.95 (s, 3H), 4.03 (dd, 2H, J=7 Hz), 4.89 (t, 2H, J=6 Hz), 5.1–5.5 (m, 6H), 5.8–6.2 (m, 1H), 8.51 (s, 1H).

Mass (m/e): 470 (M+), 429 (M+—CH$_2$CH=CH$_2$), 397 (429-S), 222 (M+—C$_{18}$H$_{33}$).

EXAMPLES 65 to 68

2-t-Butyl-3-hydroxy-7-ethoxycarbonylmethylthio-pyrazolo[4,3-d]pyrimidine obtained in Example A-23 and various tosylates were reacted and treated in the same manner as in Synthesis 1 of Example 1, whereby the following compounds of Examples 65 to 68 were obtained.

EXAMPLE 65:
2-t-Butyl-3-linoleyloxy-7-ethoxycarbonylmethylthio-pyrazolo[4,3-d]pyrimidine

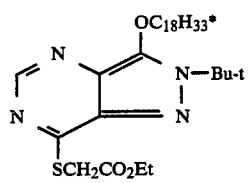

*C$_{18}$H$_{33}$: linoleyl

Starting compound: lenoleyl p-toluenesulfonate.
Yield: 60%, yellow oily substance.
pmr (CDCl$_3$) δppm: 0.89 (t, 3H, J=6 Hz), 1.21–2.08 (m, 25H), 1.72 (s, 9H), 2.77 (t, 2H, J=6 Hz), 4.14 (s, 2H), 4.23 (q, 2H, J=8 Hz), 4.91 (t, 2H, J=6 Hz), 5.35 (m, 4H), 8.46 (s, 1H).
Mass (m/e): 558 (M+).

EXAMPLE 66:
2-t-Butyl-3-n-hexadecyloxy-7-ethoxycarbonylmethylthio-pyrazolo[4,3-d]pyrimidine

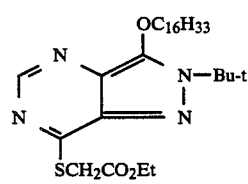

Starting compound: n-hexadecyl p-toluenesulfonate.
Yield: 51%, yellow oily substance.
pmr (CDCl$_3$) δppm: 0.88 (t, 3H, J=6 Hz), 1.20–1.94 (m, 31H), 1.72 (s, 9H), 4.14 (s, 2H), 4.23 (q, 2H, J=7 Hz), 4.91 (t, 2H, J=6 Hz), 8.46 (s, 1H).

EXAMPLE 67:
2-t-Butyl-3-n-octadecyloxy-7-ethoxycarbonylmethylthio-pyrazolo[4,3-d]pyrimidine

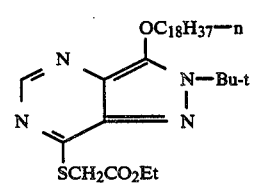

Starting compound: n-octadecyl p-toluenesulfonate.
Yield 57%.
Melting point: 33°–37° C. (Oily substance solidifies when left to stand still.).
pmr (CDCl$_3$) δppm: 0.88 (t, 3H, J=6 Hz), 1.21–1.92 (m, 35H), 1.71 (s, 9H), 4.13 (s, 2H), 4.23 (q, 2H, J=7 Hz), 4.91 (t, 2H, J=6 Hz), 8.45 (s, 1H).

EXAMPLE 68:
2-t-Butyl-3-n-dodecyloxy-7-ethoxycarbonylmethylthio-pyrazolo[4,3-d]pyrimidine

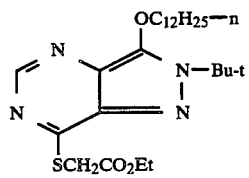

Starting compound: n-dodecyl p-toluenesulfonate.
Yield: 64%, yellow oily substance.
pmr (CDCl$_3$) δppm: 0.88 (t, 3H, J=6 Hz), 1.20–1.94 (m, 23H), 1.71 (s, 9H), 4.13 (s, 2H), 4.23 (q, 2H, J=7 Hz), 4.91 (t, 2H, J=6 Hz), 8.46 (s, 1H).

EXAMPLES 69 to 74

The following compounds of Examples 69 to 74 were prepared by the same reaction and treatment as in Example 1 except that instead of n-hexadecyl p-toluenesulfonate used in Synthesis 2 of Example 1, other tosyl compounds were employed, and instead of dimethylformamide, dimethylacetamide was employed.

EXAMPLE 69:
2-Methyl-3-erucyloxy-7-ethoxycarbonylmethylthio-pyrazolo[4,3-d]pyrimidine

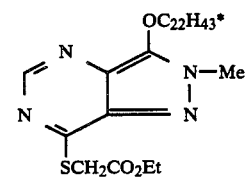

*C$_{22}$H$_{43}$: erucyl (cis-13-docosenyl)

Starting compound: erucyl p-toluenesulfonate.
Yield: 66.8%.
Melting point: <25° C., colorless solid.
pmr (CDCl$_3$) δppm: 0.7–2.2 (m, 42H), 3.96 (s, 3H), 4.13 (s, 2H), 4.23 (q, 2H, J=7 Hz), 4.89 (t, 2H, J=6 Hz), 5.3–5.4 (m, 2H), 8.49 (s, 1H).
Mass (m/e): 574 (M+).

EXAMPLE 70:
2-Methyl-3-elaidyloxy-7-ethoxycarbonylmethylthio-pyrazolo[4,3-d]pyrimidine

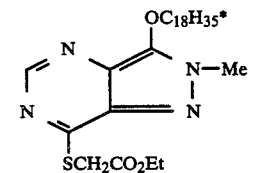

*C$_{18}$H$_{35}$: elaidyl (trans-9-octadecenyl)

Starting compound: elaidyl p-toluenesulfonate.
Yield: 71.1%.
Melting point: 37°–38° C., colorless powder.
pmr (CDCl$_3$) δppm: 0.7–2.2 (m, 34H), 3.96 (s, 3H), 4.14 (s, 2H), 4.23 (q, 2H, J=7 Hz), 4.89 (t, 2H, J=6 Hz), 5.3–5.5 (m, 2H), 8.48 (s, 1H).
Mass (m/e): 518 (M+), 431 (M+—CH$_2$CO$_2$Et), 399 (M+—SCH$_2$CO$_2$Et), 268.

EXAMPLE 71:
2-Methyl-3-petroselinyloxy-7-ethoxycarbonylmethylthio-pyrazolo[4,3-d]pyrimidine

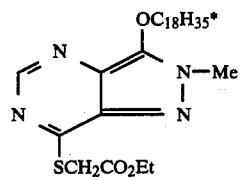

*C₁₈H₃₅: petroselinyl (cis-6-octadecenyl)

Starting compound: petroselinyl p-toluenesulfonate.
Yield: 77.2%.
Melting point: <25° C., colorless solid.
pmr (CDCl₃) δppm: 0.7–2.2 (m, 34H), 3.96 (s, 3H), 4.14 (s, 2H), 4.22 (q, 2H, J=7 Hz), 4.89 (t, 2H, J=6 Hz), 5.3–5.5 (m, 2H), 8.48 (s, 1H).
Mass (m/e): 518 (M+), 431 (M+—CH₂CO₂Et), 399 (M+—SCH₂CO₂Et), 268, 87.

EXAMPLE 72:
2-Methyl-3-vaccenyloxy-7-ethoxycarbonylmethylthio-pyrazolo[4,3-d]pyrimidine

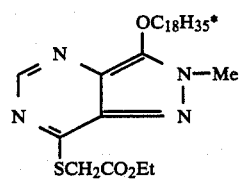

*C₁₈H₃₅: vaccenyl (trans-11-octadecenyl)

Yield: 63.7%.
Melting point: <25° C., pale yellow solid.
pmr (CDCl₃) δppm: 0.7–2.2 (m, 34H), 3.96 (s, 3H), 4.14 (s, 2H), 4.23 (q, 2H, J=7 Hz), 4.89 (t, 2H, J=6 Hz), 5.3–5.5 (m, 2H), 8.49 (s, 1H).
Mass (m/e): 518 (M+), 431 (M+—CH₂CO₂Et), 399 (M+—SCH₂CO₂Et), 268.

EXAMPLE 73:
2-Methyl-3-(10-undecenyloxy)-7-ethoxycarbonylmethylthio-pyrazolo[4,3-d]pyrimidine

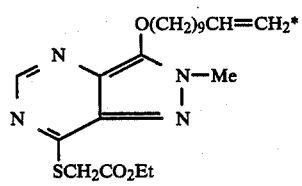

Starting compound: 10-undecenyl p-toluenesulfonate.
Yield: 77.9%, pale yellow oily substance.
pmr (CDCl₃) δppm: 1.2–2.2 (m, 19H), 3.95 (s, 3H), 4.14 (s, 2H), 4.22 (q, 2H, J=7 Hz), 4.88 (t, 2H, J=6 Hz), 4.9–5.1 (m, 2H), 5.6–6.0 (m, 1H), 8.48 (s, 1H).
Mass (m/e): 420 (M+), 375 (M+—OEt), 268.

EXAMPLE 74:
2-Methyl-3-(3-decynyloxy)-7-ethoxycarbonylmethylthio-pyrazolo[4,3-d]pyrimidine

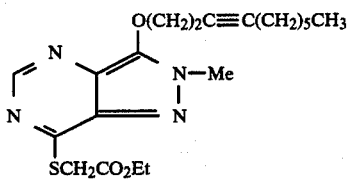

Starting compound: 3-decynyl p-toluenesulfonate.
Yield: 65.6%, light brown oily substance.
pmr (CDCl₃) δppm: 0.7–1.7 (m, 14H), 2.0–2.3 (m, 2H), 2.6–2.8 (m, 2H), 3.98 (s, 3H), 4.14 (s, 2H), 4.22 (q, 2H, J=7 Hz), 4.92 (t, 2H, J=6 Hz), 8.49 (s, 1H).
Mass (m/e): 404 (M+), 285, 268.

Now, there will be given Examples for formulations containing antihyperlipidemic compounds of the present invention.

Formulation Example 1: Tablets

| Composition (4,000 tablets) | |
|---|---|
| Compound of Example 1 | 500 (g) |
| Potato starch | 334 |
| Carboxymethyl cellulose | 87.5 |
| Polyvinyl alcohol | 61 |
| Magnesium stearate | 17.5 |
| | 1,000 |

The above ingredients in the respective amounts were introduced into a twin shell mixer and uniformly mixed. This powder mixture was tableted by a direct compression method to obtain tablets having a weight of 250 mg per tablet.

Formulation Example 2: Capsules

| Composition (1,000 capsules) | |
|---|---|
| Compound of Example 10 | 250 (g) |
| Olive oil | 250 |
| | 500 |

The above ingredients in the respective amounts were uniformly mixed. This powder mixture was packed in soft gelatin capsules in an amount of 500 mg per capsule, and dried.

Formulation Example 3: Granules

| Composition (1,000 packages) | |
|---|---|
| Compound of Example 15 | 100 (g) |
| Silicic anhydride | 80 |
| Crystalline cellulose | 180 |
| Lactose | 130 |
| Magnesium stearate | 10 |
| | 500 |

The above ingredients in the respective amounts were uniformly mixed, then granulated and packaged in an amount of 500 mg per package.

Formulation Example 4: Suppository

| Composition (1,000 pcs) | |
|---|---|
| Compound of Example 9 | 200 (g) |
| Cacao butter | 1,000 |
| | 1,200 |

The above ingredients in the respective amounts were uniformly melted at 38° C., and poured into a casting mold for suppository which was preliminarily cooled. The weight per piece of suppository was 1.2 g.

We claim:

1. A pyrazolo[4,3-d]pyrimidine derivative having the formula:

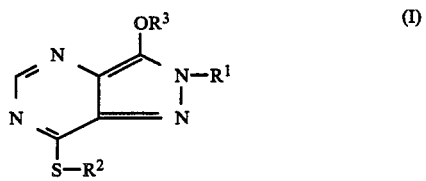

wherein $R^1$ is lower alkyl or phenyl, $R^2$ is —A—$CO_2R^{21}$ (wherein A is alkylene having from 1 to 10 carbon atoms which is unsubstituted or substituted by alkyl having from 1 to 3 carbon atoms, and $R^{21}$ is lower alkyl having from 1 to 4 carbon atoms), —$CH_2$CO-phenyl, a saturated or unsaturated, straight chain or branched aliphatic group having from 3 to 16 carbon atoms, phenyl-lower alkyl, —$CH_2$CN, chloro substituted phenyl-lower alkyl or

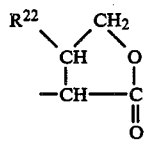

(wherein $R^{22}$ is hydrogen or lower alkyl), and $R^3$ is a saturated or unsaturated, straight chain or branched aliphatic group having from 2 to 22 carbon atoms, phenyl-lower alkyl, benzyloxy substituted phenyl-lower alkyl, lower alkyl substituted or unsubstituted 2-(phenylmethyloxy)ethyl, cyclohexylcyclohexyl, methylcyclohexyl, 3-thia-n-heptyl, 3,6-dioxa-n-decyl, 4-oxo-n-pentyl or 2-hydroxyethyl.

2. The pyrimidine derivative according to claim 1, wherein $R^1$ is methyl, $R^2$ is —$CH_2CO_2R^{21}$ (wherein $R^{21}$ is as defined above), —$C(CH_3)_2CO_2R^{21}$ (wherein $R^{21}$ is as defined above),

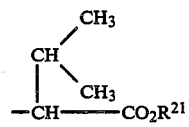

(wherein $R^{21}$ is as defined above), —$(CH_2)_3CO_2R^{21}$ (wherein $R^{21}$ is as defined above), —$CH_2$CO-phenyl, —$CH_2$CN or alkyl having from 3 to 16 carbon atoms, and $R^3$ is a saturated or unsaturated, straight chain or branched aliphatic group having from 12 to 22 carbon atoms.

3. The pyrimidine derivative according to claim 1, wherein $R^1$ is a phenyl group, $R^2$ is —$CH_2CO_2R^{21}$ (wherein $R^{21}$ is as defined above) or —$C(CH_3)_2CO_2R^{21}$ (wherein $R^{21}$ is as defined above), and $R^3$ is a saturated or unsaturated, straight chain or branched aliphatic group having 7 to 20 carbon atoms.

4. The pyrimidine derivative according to claim 1, wherein $R^1$ is t-butyl, $R^2$ is —$CH_2CO_2R^{21}$ (wherein $R^{21}$ is as defined above), and $R^3$ is a saturated or unsaturated straight chain or branched aliphatic group having from 14 to 22 carbon atoms.

5. The pyrimidine derivative according to claim 1, wherein $R^1$ is methyl, $R^2$ is —$CH_2CO_2R^{21}$ (wherein $R^{21}$ is as defined above), and $R^3$ is linoleyl, oleyl, linolenyl or straight chain alkyl having 14 to 22 carbon atoms.

6. 2-Methyl-3-linoleyloxy-7-ethoxycarbonylmethylthio-pyrazolo[4,3-d]pyrimidine according to claim 1.

7. 2-Methyl-3-linolenyloxy-7-ethoxycarbonylmethylthio-pyrazolo[4,3-d]pyrimidine according to claim 1.

8. 2-Methyl-3-oleyloxy-7-ethoxycarbonylmethylthio-pyrazolo[4,3-d]pyrimidine according to claim 1.

9. 2-Methyl-3-n-hexadecyloxy-7-ethoxycarbonylmethylthio-pyrazolo[4,3-d]pyrimidine according to claim 1.

10. 2-Methyl-3-linoleyloxy-7-cyanomethylthio-pyrazolo[4,3-d]pyrimidine according to claim 1.

11. 2-Methyl-3-linoleyloxy-7-(3-ethoxycarbonylpropylthio)-pyrazolo[4,3-d]pyrimidine according to claim 1.

12. An antihyperlipidemic agent comprising an effective amount of the pyrimidine derivative of the formula I as defined in claim 1 and a pharmaceutically acceptable carrier.

13. A pyrazolo[4,3-d]pyrimidine derivative having the formula:

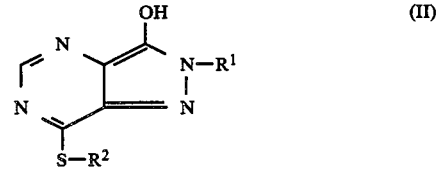

wherein $R^1$ is lower alkyl or phenyl, $R^2$ is —A—$CO_2R^{21}$ (wherein A is alkylene having from 1 to 10 carbon atoms which is unsubstituted or substituted by alkyl having from 1 to 3 carbon atoms, and $R^{21}$ is lower alkyl having 1 to 4 carbon atoms), —$CH_2$CO—phenyl, a saturated or unsaturated, straight chain or branched aliphatic group having from 3 to 16 carbon atoms, phenyl-lower alkyl, —$CH_2$CN, chloro substituted phenyl-lower alkyl or

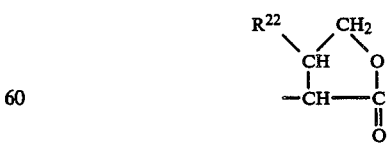

wherein $R^{22}$ is hydrogen or lower alkyl.

* * * * *